US012702837B2

(12) United States Patent
Litvak et al.

(10) Patent No.: US 12,702,837 B2
(45) Date of Patent: Aug. 11, 2026

(54) DETERMINING ESTIMATED NEURAL THRESHOLD WITH ECAP SIGNALS

(71) Applicant: Medtronic, Inc., Minneapolis, MN (US)

(72) Inventors: Leonid M. Litvak, Bet Shemesh (IL); David A. Dinsmoor, North Oaks, MN (US); Juan G. Hincapie, Maple Grove, MN (US); Jeffery M. Kramer, St. Louis Park, MN (US); Jerel K. Mueller, St. Paul, MN (US); Joshua J. Nedrud, Roseville, MN (US); Malgorzata M. Straka, Blaine, MN (US)

(73) Assignee: Medtronic, Inc., Minneapolis, MN (US)

( * ) Notice: Subject to any disclaimer, the term of this patent is extended or adjusted under 35 U.S.C. 154(b) by 271 days.

(21) Appl. No.: 18/270,810

(22) PCT Filed: Jan. 7, 2022

(86) PCT No.: PCT/US2022/011690

§ 371 (c)(1),
(2) Date: Jul. 3, 2023

(87) PCT Pub. No.: WO2022/150638

PCT Pub. Date: Jul. 14, 2022

(65) Prior Publication Data

US 2024/0293676 A1 Sep. 5, 2024

Related U.S. Application Data

(60) Provisional application No. 63/135,342, filed on Jan. 8, 2021.

(51) Int. Cl.
*A61N 1/36* (2006.01)

(52) U.S. Cl.
CPC ..... *A61N 1/36139* (2013.01); *A61N 1/36146* (2013.01)

(58) Field of Classification Search
CPC ............ A61N 1/36139; A61N 1/36178; A61N 1/36039; A61N 1/36175; A61N 1/3615;
(Continued)

(56) References Cited

U.S. PATENT DOCUMENTS 6,266,558 B1 7/2001 Gozani et al.
8,165,687 B2 4/2012 Cornejo Cruz et al.
(Continued)

FOREIGN PATENT DOCUMENTS

EP 1972359 A2 9/2008
EP 3024540 A1 6/2016
(Continued)

OTHER PUBLICATIONS

Abbas et al., "Channel interaction in cochlear implant users evaluated using the electrically evoked compound action potential", Audiology and Neurotology, vol. 9, No. 4, S. Karger AG, Basel, Feb. 10, 2004, pp. 203-213.
(Continued)

*Primary Examiner* — Deborah L Malamud
(74) *Attorney, Agent, or Firm* — Shumaker & Sieffert, P.A.

(57) ABSTRACT

Systems, devices, and techniques are described for analyzing evoked compound action potential (ECAP) signals to determine an estimated neural threshold of a patient. In one example, a method includes controlling, by processing circuitry, delivery of a plurality of stimulation pulses to a patient, wherein each stimulation pulse of the plurality of stimulation pulses is at least partially defined by a different respective value of a stimulation parameter; receiving, by the processing circuitry, ECAP signal information, wherein
(Continued)

the ECAP signal information comprises ECAP signals sensed by sensing circuitry and elicited by the plurality of stimulation pulses; determining, by the processing circuitry and based on the ECAP signal information, ECAP characteristic values for each of the ECAP signals elicited by the plurality' of stimulation pulses; and determining, by the processing circuitry and based on the ECAP characteristic values, an estimated neural threshold of the patient.

21 Claims, 15 Drawing Sheets

(58) Field of Classification Search
CPC ............ A61N 1/36164; A61N 1/37241; A61N 1/36128; A61N 1/36146; A61N 1/36157; A61B 5/24; A61B 5/388; A61B 5/4041; A61B 5/1106; A61B 5/4836; A61B 5/4848; A61B 5/6877; A61B 5/7282; A61B 5/05; A61B 5/053; A61B 5/395
See application file for complete search history.

(56) References Cited

U.S. PATENT DOCUMENTS

| | | | |
|---|---|---|---|
| 9,381,356 B2 | 7/2016 | Parker et al. | |
| 10,183,168 B2 | 1/2019 | Baru et al. | |
| 11,337,658 B2 | 5/2022 | Single | |
| 2005/0261748 A1 | 11/2005 | Van Dijk | |
| 2010/0249643 A1 | 9/2010 | Gozani et al. | |
| 2011/0245891 A1 | 10/2011 | Fritsch et al. | |
| 2013/0274827 A1 | 10/2013 | Smoorenburg | |
| 2015/0005842 A1 | 1/2015 | Lee et al. | |
| 2015/0032181 A1 | 1/2015 | Baynham et al. | |
| 2016/0157769 A1 | 6/2016 | Min et al. | |
| 2016/0199642 A1 | 7/2016 | Schwarz et al. | |
| 2016/0287182 A1 | 10/2016 | Single | |
| 2017/0361101 A1 | 12/2017 | Single | |
| 2019/0099602 A1 | 4/2019 | Esteller et al. | |
| 2019/0175904 A1 | 6/2019 | Baru et al. | |
| 2019/0275331 A1* | 9/2019 | Zhu | A61N 1/36192 |
| 2019/0388692 A1 | 12/2019 | Dinsmoor et al. | |
| 2019/0388695 A1 | 12/2019 | Dinsmoor et al. | |
| 2020/0029914 A1 | 1/2020 | Single | |
| 2020/0179688 A1 | 6/2020 | Su | |
| 2020/0316391 A1 † | 10/2020 | Kibler | |

FOREIGN PATENT DOCUMENTS

| | | |
|---|---|---|
| EP | 3337555 A1 | 6/2018 |
| WO | 2004084722 A1 | 10/2004 |
| WO | 2015013398 A1 | 1/2015 |
| WO | 2015095665 A1 | 6/2015 |
| WO | 2016090436 A1 | 6/2016 |
| WO | 2016161484 A1 | 10/2016 |
| WO | 2017028906 A1 | 2/2017 |
| WO | 2017173493 A1 | 10/2017 |
| WO | 2021126433 A1 † | 6/2021 |
| WO | 2022126057 A1 | 6/2022 |

OTHER PUBLICATIONS

Adenis et al., "ECAP growth function to increasing pulse amplitude or pulse duration demonstrates large inter-animal variability that is reflected in auditory cortex of the guinea pig", Plos One, vol. 13, No. 8, Aug. 2, 2018, 24 pp., https://doi.org/10.1371/journal.pone.0201771.

Akin et al., "Results of a multicenter clinical study evaluating a new smart algorithm to measure neural response imaging", Otology & Neurotology, vol. 33, No. 5, Otology & Neurotology, Inc, Jul. 1, 2012, pp. 736-739.

Brown et al., "Electrically evoked whole nerve action potentials: data from human cochlear implant users", The Journal of the Acoustical Society of America, vol. 88, No. 3, Acoustical Society of America, Sep. 1, 1990, pp. 1385-1391.

Brown et al., "Preliminary experience with Neural Response Telemetry in the Nucleus CI24M cochlear implant", The American Journal of Otology, vol. 19, No. 3, The American Journal of Otology, Inc, May 1, 1998, pp. 320-327.

Cedeno et al., "Spinal cord stimulation using differential target multiplexed programming modulates neural cell-specific transcriptomes in an animal model of neuropathic pain", Molecular Pain, vol. 16, Sage, Oct. 13, 2020, 8 pp., doi: 10.1177/1744806920964360.

Chakravarthy et al., "Sensing Evoked Compound Action Potentials from the Spinal Cord: Novel Preclinical and Clinical Considerations for the Pain Management Researcher and Clinician", Journal of Pain Research, vol. 13, Dovepress, Dec. 4, 2020, pp. 3269-3279, doi.org/10.2147/JPR.S289098.

He et al., "Perception threshold and electrode position for spinal cord stimulation", PAIN, vol. 59, No. 1, Elsevier Science B.V., Feb. 23, 1994, pp. 55-63.

Holsheimer et al., "MR Asessment of the Normal Position of the Spinal Cord in the Spinal Cord", American Society of Neuroradiology, vol. 15, No. 5, May 1994, pp. 951-959.

International Preliminary Report on Patentability from International Application No. PCT/US2022/011690 dated Jul. 20, 2023, 7 pp.

International Search Report and Written Opinion of International Application No. PCT/US2022/011690, dated Jun. 1, 2022, 16 pp.

Laird-Wah, "Improving Spinal Cord Stimulation", Graduate School of Biomedical Engineering, University of New South Wales, Aug. 2015, 273 pp.

Lempka et al., "Patient-Specific Analysis of Neural Activation During Spinal Cord Stimulation for Pain", Neuromodulation: Technology at the Neural Interface, vol. 23, PubMed, Aug. 28, 2019, pp. 572-581, doi: 10.1111/ner.13037.

Medtronic, "Efficio Pump Management Software", Medtronic, May 2022, 3 pp., Retrieved from the Internet on Feb. 12, 2024 from URL: https://www.medtronic.com/us-en/c/pain-therapies/efficio.html?cmpid=vanity_url_medtronic_com_Efficio_RTG_Pain_FY20.

Mekhail et al., "Evoked compound action potential recording to further understand effect of titrating medication with spinal cord stimulation—case study", EFIC congress, Sep. 3, 2019, 1 pp.

Mekhail et al., "Long-term safety and efficacy of closed-loop spinal cord stimulation to treat chronic back and leg pain (Evoke): a double-blind, randomised, controlled trial. Lancet Neurol", The Lancet Neurology, vol. 19, No. 2, Elsevier Ltd, Feb. 1, 2020, pp. 123-134.

Melzack et al., "Pain Mechanisms: A New Theory", Science, vol. 150, No. 3699, Nov. 19, 1965, pp. 971-979, doi: 10.1126/science.150.3699.971.

Miller et al., "An improved method of reducing stimulus artifact in the electrically evoked whole-nerve potential", Ear and hearing, vol. 21, No. 4, Lippincott Williams & Wilkins, Aug. 1, 2000, pp. 280-290.

Miller et al., "Electrically evoked compound action potentials of guinea pig and cat: responses to monopolar, monophasic stimulation. Hear", Hearing research, vol. 119, No. 1-2, Elsevier, May 1, 1998, pp. 142-154.

Morsnowski et al., "Measuring the refractoriness of the electrically stimulated auditory nerve", Audiology and Neurotology, vol. 11, No. 6, S. Karger AG, Basel, Sep. 27, 2006, pp. 389-402.

Nehme et al., "Measures of the electrically evoked compound action potential threshold and slope in HiRes 90KTM users", Cochlear implants international, vol. 15, No. 1, W.S. Maney & Son Ltd, Jan. 6, 2014, pp. 53-60.

Parker et al., "Compound action potentials recorded in the human spinal cord during neurostimulation for pain relief", vol. 153, No. 3, Elsevier B.V., Nov. 21, 2011, pp. 593-601.

Parker et al., "Evoked compound action potentials reveal spinal cord dorsal column neuroanatomy", Neuromodulation: Technology at the Neural Interface, International Neuromodulation Society, Mar. 19, 2019, pp. 82-95.

(56) References Cited

OTHER PUBLICATIONS

Ren et al., "Neuron-glia crosstalk gets serious: role in pain hypersensitivity", Current Opinion in Anesthesiology, vol. 21, No. 5, Oct. 2008, pp. 570-579, doi: 10.1097/ACO.0b013e32830edbdf.
Russo et al., "Effective Relief of Pain and Associated Symptoms With Closed-Loop Spinal Cord Stimulation System: Preliminary Results of the Avalon Study", Neuromodulation: Technology at the Neural Interface, vol. 21, No. 1, International Neuromodulation Society, Jul. 17, 2017, pp. 38-47.
Sankarasubramanian et al., "Triple Leads Programmed to Perform as Longitudinal Guarded Cathodes in Spinal Cord Stimulation: A Modeling Study", Neuromodulation: Technology at the Neural Interface, vol. 14, No. 5, Sep. 2011, pp. 401-411, doi: 10.1111/j.1525-1403.2011.00383.x.
Shealy et al., "Electrical Inhibition of Pain by Stimulation of the Dorsal Columns Preliminary Clinical Report", Anesthesia & Analgesia, vol. 46, No. 4, International Anesthesia Research Society, Jul. 1967, pp. 489-491.
Single et al., "Cause of Pulse Artefacts Inherent to the Electrodes of Neuromodulation Implants", IEEE Transactions on Neural Systems and Rehabilitation Engineering, vol. 26, No. 10, EMB, Oct. 2018, pp. 2078-2083, DOI: 10.1109/TNSRE.2018.2870169.
Stanslaski et al., "Design and validation of a fully implantable, chronic, closed-loop neuromodulation device with concurrent sensing and stimulation", IEEE Transactions on Neural Systems and Rehabilitation Engineering, vol. 20, No. 4, IEEE, Jan. 23, 2012, pp. 410-421.
U.S. Appl. No. 18/546,917, filed Feb. 21, 2022, naming inventors Dinsmoor et al.
Van De Honert et al., "Characterization of the electrically evoked auditory brainstem response (EABR) in cats and humans", Hearing research, Elsevier Science Publishers B.V., Oct. 31, 1985, pp. 109-126.
Wu et al., "Spinal Cord Stimulation", Clinicalgate, Feb. 27, 2015, 15 pp., URL: https://clinicalgate.com/spinal-cord-stimulation-6/.
Office Action from U.S. Appl. No. 18/546,917 dated Sep. 25, 2025, 13 pp.
Notice of Allowance from U.S. Appl. No. 18/546,917 dated Feb. 19, 2026.
Communication pursuant to Article 94(3) EPC from counterpart European Application No. 22702349.6 dated Dec. 15, 2025, 6 pp.
Response to Office Action dated Sep. 25, 2025 from U.S. Appl. No. 18/546,917, filed Dec. 17, 2025, 10 pp.
Corrected Notice of Allowance from U.S. Appl. No. 18/546,917 dated Mar. 18, 2026, 2 pp.
First Office Action and Search Report, and translation thereof, from counterpart Chinese Application No. 202280009246.8 dated Apr. 30, 2026.

* cited by examiner
† cited by third party

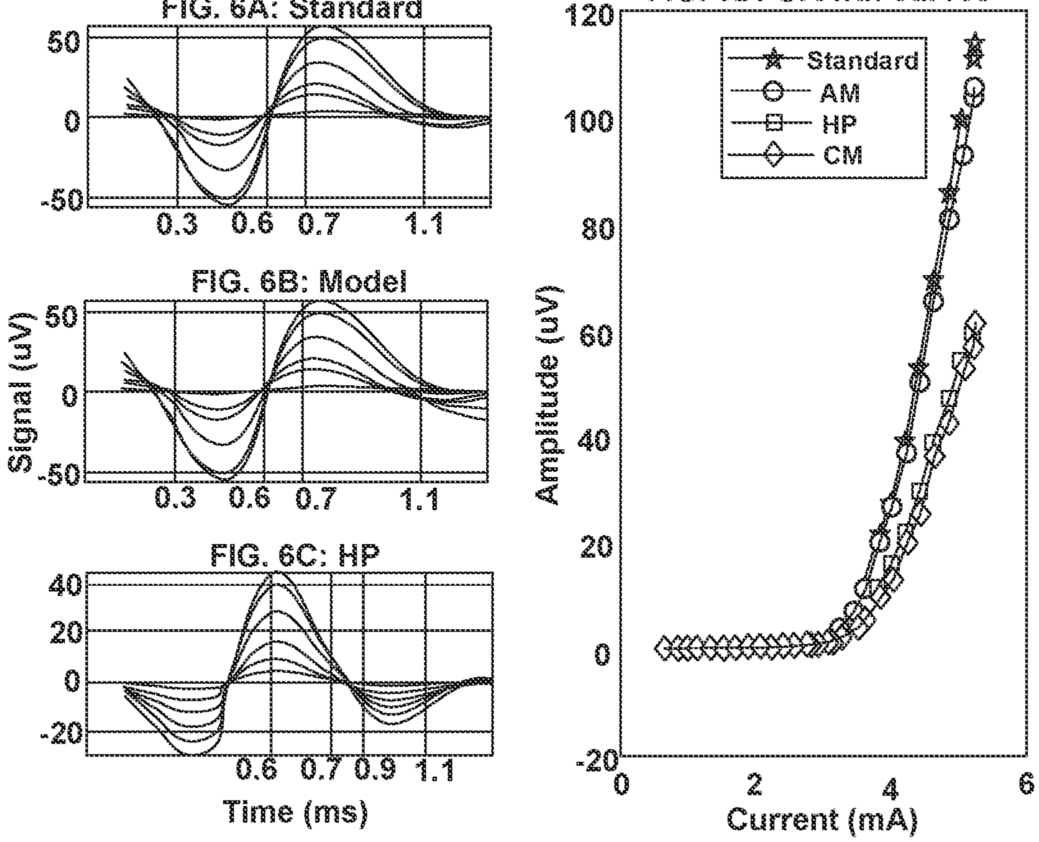
FIG. 6A: Standard
50
0
-50
0.3 0.6 0.7 1.1
FIG. 6B: Model
Signal (uV)
50
0
-50
0.3 0.6 0.7 1.1
FIG. 6C: HP
40
20
0
-20
0.6 0.7 0.9 1.1
Time (ms)
FIG. 6D: Growth curves
Standard
AM
HP
CM
120
100
80
60
40
20
0
-20
Amplitude (uV)
0 2 4 6
Current (mA)

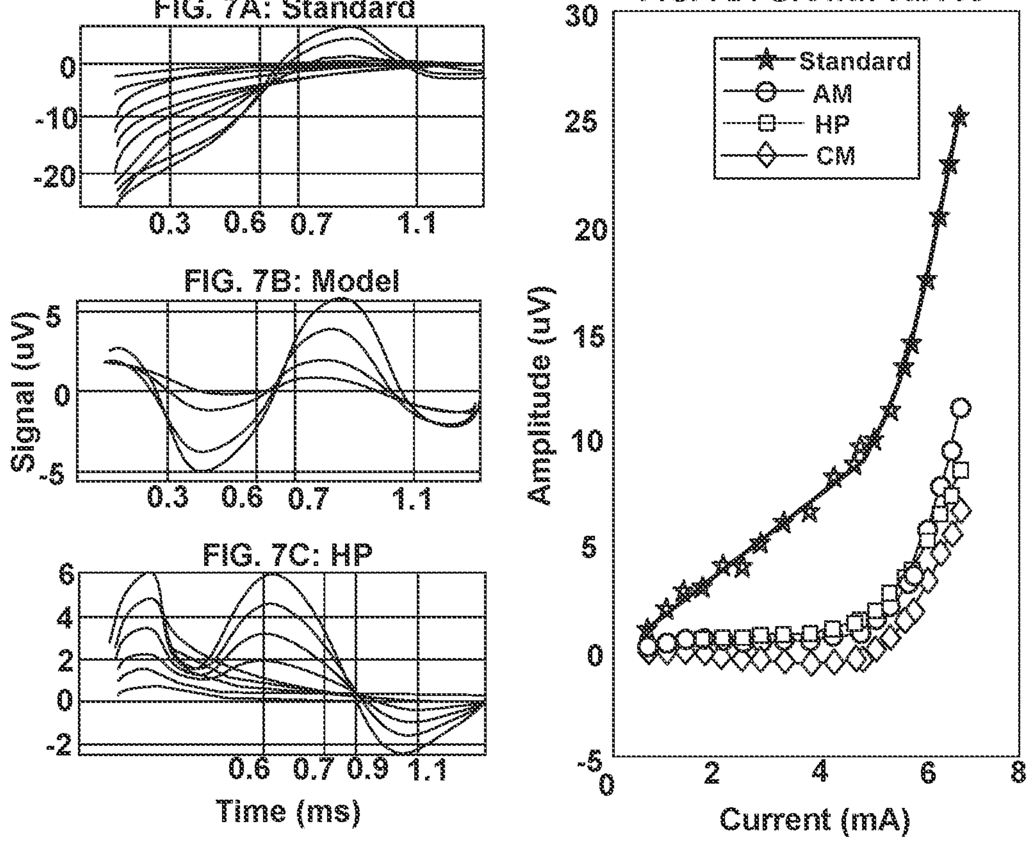
FIG. 7A: Standard
0
-10
-20
0.3 0.6 0.7 1.1
FIG. 7B: Model
Signal (uV)
5
0
-5
0.3 0.6 0.7 1.1
FIG. 7C: HP
6
4
2
0
-2
0.6 0.7 0.9 1.1
Time (ms)
FIG. 7D: Growth curves
Standard
AM
HP
CM
Amplitude (uV)
30
25
20
15
10
5
0
-5
0
2
4
6
8
Current (mA)

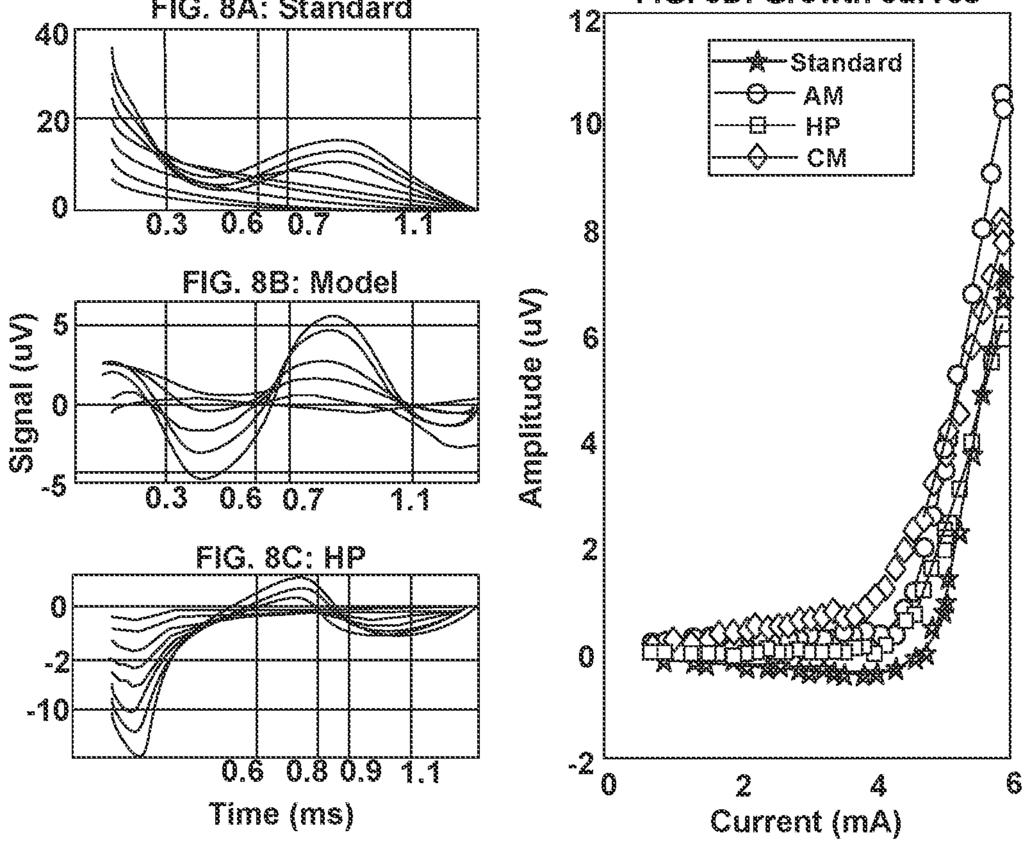
FIG. 8A: Standard
40
20
0
0.3 0.6 0.7 1.1
FIG. 8B: Model
Signal (uV)
5
0
-5
0.3 0.6 0.7 1.1
FIG. 8C: HP
0
-2
-10
0.6 0.8 0.9 1.1
Time (ms)
FIG. 8D: Growth curves
Standard
AM
HP
CM
Amplitude (uV)
12
10
8
6
4
2
0
-2
0 2 4 6
Current (mA)

DETERMINING ESTIMATED NEURAL THRESHOLD WITH ECAP SIGNALS

This application is a national stage entry of International Patent Application No. PCT/US2022/011690, filed Jan. 7, 2022, which claims the benefit of and priority to U.S. Provisional Application Ser. No. 63/135,342, filed on Jan. 8, 2021, the entire content of applications PCT/US2022/011690 and 63/135,342 are incorporated herein by reference.

TECHNICAL FIELD

This disclosure generally relates to sensing physiological parameters, and more specifically, analysis of a sensed signal indicative of a physiological parameter.

BACKGROUND

Medical devices may be external or implanted and may be used to deliver electrical stimulation therapy to patients via various tissue sites to treat a variety of symptoms or conditions such as chronic pain, tremor, Parkinson's disease, epilepsy, urinary or fecal incontinence, sexual dysfunction, obesity, or gastroparesis. A medical device may deliver electrical stimulation therapy via one or more leads that include electrodes located proximate to target locations associated with the brain, the spinal cord, pelvic nerves, peripheral nerves, or the gastrointestinal tract of a patient. Stimulation proximate the spinal cord, proximate the sacral nerve, within the brain, and proximate peripheral nerves are often referred to as spinal cord stimulation (SCS), sacral neuromodulation (SNM), deep brain stimulation (DBS), and peripheral nerve stimulation (PNS), respectively.

Electrical stimulation may be delivered to a patient by the medical device in a train of electrical pulses, and parameters of the electrical pulses may include a frequency, an amplitude, a pulse width, and a pulse shape. An evoked compound action potential (ECAP) is synchronous firing of a population of neurons which occurs in response to the application of a stimulus including, in some cases, an electrical stimulus by a medical device. The ECAP may be detectable as being a separate event from the stimulus itself, and the ECAP may reveal characteristics of the effect of the stimulus on the nerve fibers.

SUMMARY

In general, systems, devices, and techniques are described for analyzing evoked compound action potential (ECAP) signals and for estimating a neural threshold of a patient using the analyzed ECAP signals to assess the effect of a delivered electrical stimulation signal. A system may use the estimated neural threshold and/or one or more characteristics of the ECAP signal to control subsequent electrical stimulation delivered to a patient.

Devices and systems described herein may analyze an ECAP signal, which may include removing stimulation artifact components from the ECAP signal, prior to determining one or more characteristics of the ECAP signal. In this manner, the background noise or other artifacts associated with the stimulus may have a reduced effect on the measurement of the characteristics of the ECAP signal. An IMD or programmer may determine an estimated neural threshold based on the ECAP signal characteristics and adjust one or more parameter values that define subsequent electrical stimulation based on the estimated neural threshold and/or the ECAP characteristic value.

In some examples, one or more parameters for a therapy, such as for SCS stimulation, may be programmed based on a patient sensory threshold that may be correlated with, or similar to, the estimated threshold for neural activation (also referred to as "neural threshold" herein). In some examples, the programming and/or closed-loop control of SCS stimulation may be based on the estimated neural threshold. In one or more examples, determination of the estimated neural threshold may be performed by the system and/or with the assistance of a user (e.g., the patient). For example, the programmer may signal the patient to stay in a certain position during delivery of stimulation and the recording of respective ECAP signals. The programmer may then determine one or more growth curves using the techniques herein and the processing circuitry and determine an estimated neural threshold.

In one example, this disclosure describes a method that includes: controlling, by processing circuitry, delivery of a plurality of stimulation pulses to a patient, wherein each stimulation pulse of the plurality of stimulation pulses is at least partially defined by a different respective value of a stimulation parameter; receiving, by the processing circuitry, ECAP signal information, wherein the ECAP signal information comprises ECAP signals sensed by sensing circuitry and elicited by the plurality of stimulation pulses; determining, by the processing circuitry and based on the ECAP signal information, ECAP characteristic values for each of the ECAP signals elicited by the plurality of stimulation pulses; and determining, by the processing circuitry and based on the ECAP characteristic values, an estimated neural threshold of the patient.

In another example, this disclosure describes a system that includes processing circuitry configured to: control, by processing circuitry, delivery of a plurality of stimulation pulses to a patient, wherein each stimulation pulse of the plurality of stimulation pulses is at least partially defined by a different respective value of a stimulation parameter; receive, by the processing circuitry, ECAP signal information, wherein the ECAP signal information comprises ECAP signals sensed by sensing circuitry and elicited by the plurality of stimulation pulses; determine, by the processing circuitry and based on the ECAP signal information, ECAP characteristic values for each of the ECAP signals elicited by the plurality of stimulation pulses; and determine, by the processing circuitry and based on the ECAP characteristic values, an estimated neural threshold of the patient.

In another example, this disclosure describes a computer-readable storage medium including instructions that, when executed, cause processing circuitry to: deliver of a plurality of stimulation pulses to a patient, wherein each stimulation pulse of the plurality of stimulation pulses is at least partially defined by a different respective value of a stimulation parameter; receive, by the processing circuitry, ECAP signal information, wherein the ECAP signal information comprises ECAP signals sensed by sensing circuitry and elicited by the plurality of stimulation pulses; determine, by the processing circuitry and based on the ECAP signal information, ECAP characteristic values for each of the ECAP signals elicited by the plurality of stimulation pulses; and determine, by the processing circuitry and based on the ECAP characteristic values, an estimated neural threshold of the patient.

The summary is intended to provide an overview of the subject matter described in this disclosure. It is not intended to provide an exclusive or exhaustive explanation of the systems, device, and methods described in detail within the accompanying drawings and description below. Further details of one or more examples of this disclosure are set forth in the accompanying drawings and in the description below. Other features, objects, and advantages will be apparent from the description and drawings, and from the claims.

BRIEF DESCRIPTION OF DRAWINGS

FIG. 6A is a graph of the waveforms $V_i(t)$ of an example standard method of determining ECAP characteristic values for an example response recorded from a human subject.

FIG. 6B is a graph of the waveforms $V_i(t)$ of an example artifact method of determining ECAP characteristic values for an example response recorded from a human subject.

FIG. 6C is a graph of the waveforms $V_i(t)$ of an example high-pass filter method of determining ECAP characteristic values for an example response recorded from a human subject.

FIG. 6D is an example growth curve of ECAP characteristic values using four different methods for determining ECAP characteristic values.

FIG. 7A is a graph of the waveforms $V_i(t)$ of an example standard method of determining ECAP characteristic values for an example response recorded from a human subject.

FIG. 7B is a graph of the waveforms $V_i(t)$ of an example artifact method of determining ECAP characteristic values for an example response recorded from a human subject.

FIG. 7C is a graph of the waveforms $V_i(t)$ of an example high-pass filter method of determining ECAP characteristic values for an example response recorded from a human subject.

FIG. 7D is an example growth curve of ECAP characteristic values using four different methods for determining ECAP characteristic values.

FIG. 8A is a graph of the waveforms $V_i(t)$ of an example standard method of determining ECAP characteristic values for an example response recorded from a human subject.

FIG. 8B is a graph of the waveforms $V_i(t)$ of an example artifact method of determining ECAP characteristic values for an example response recorded from a human subject.

FIG. 8C is a graph of the waveforms $V_i(t)$ of an example high-pass filter method of determining ECAP characteristic values for an example response recorded from a human subject.

FIG. 8D is an example growth curve of ECAP characteristic values using four different methods for determining ECAP characteristic values.

DETAILED DESCRIPTION

Figure 1:
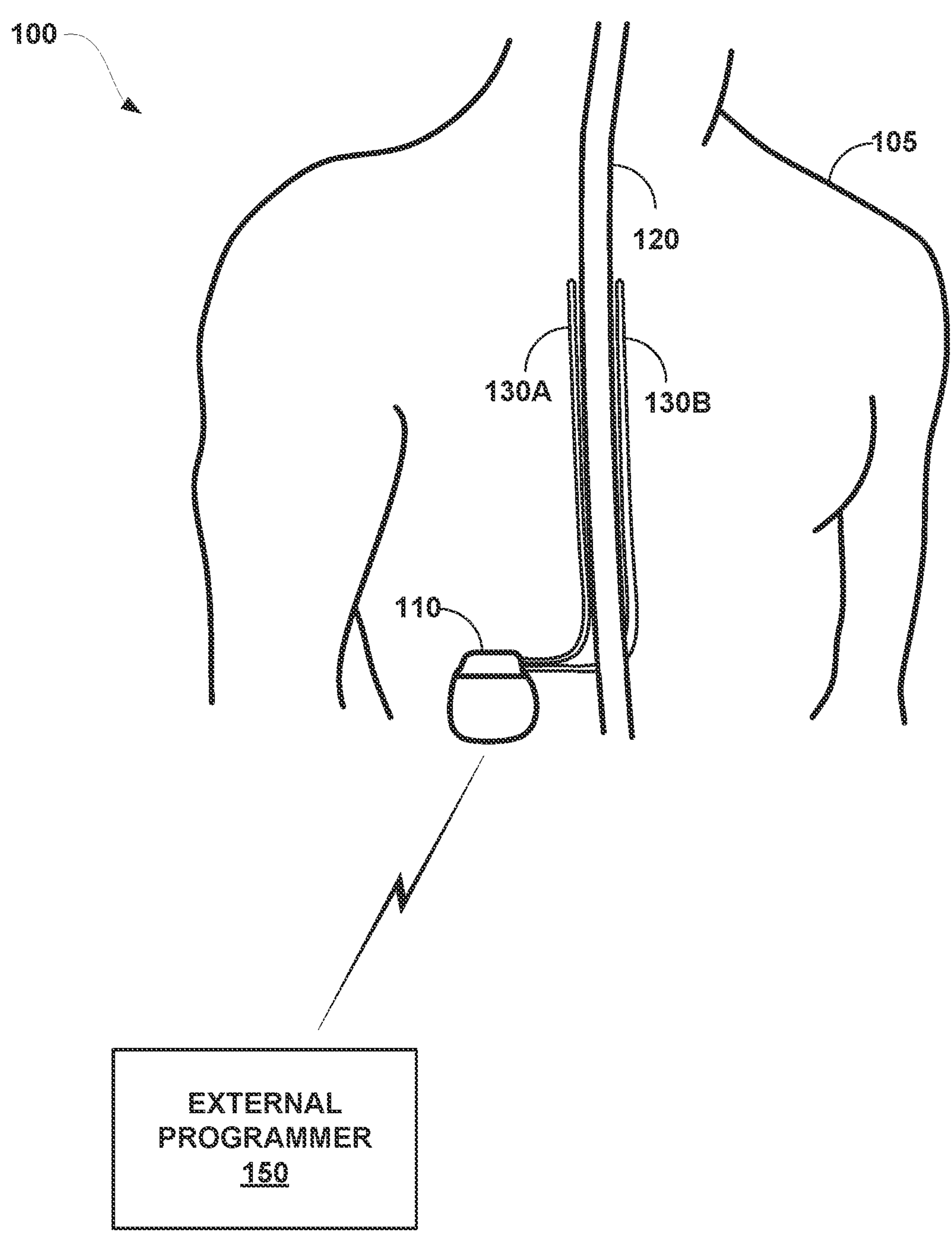
FIG. 1 is a conceptual diagram illustrating an example system that includes an implantable medical device (IMD) configured to deliver spinal cord stimulation (SCS) therapy and an external programmer.

The disclosure describes examples of medical devices, systems, and techniques for analyzing evoked compound action potential (ECAP) signals to determine an estimated neural threshold for stimulation, and using the estimated neural threshold for evaluation, programming, and/or control of stimulation therapy based on ECAP signals. Electrical stimulation therapy is typically delivered to a target tissue (e.g., nerves of the spinal cord or muscle) of a patient via two or more electrodes. Parameters of the electrical stimulation therapy (e.g., electrode combination, voltage or current amplitude, pulse width, pulse frequency, etc.) are selected by a clinician and/or the patient to provide relief from various symptoms, such as pain, systems from nervous system disorders, symptoms from muscle disorders, etc. Various thresholds, such as a perception threshold and/or discomfort threshold, may be determined for the patient and used to select and/or recommend parameters of the stimulation therapy.

ECAPs are a measure of neural recruitment, because each ECAP signal represents the superposition of electrical potentials generated from a population of axons firing in response to an electrical stimulus (e.g., a stimulation pulse). Changes in a characteristic (e.g., an amplitude of a portion of the signal or area under the curve of the signal) of an ECAP signal occurs as a function of how many axons have been activated by the delivered stimulation pulse. For a given set of parameter values that define the stimulation pulse and a given distance between the electrodes and target nerve, the detected ECAP signal may have a certain characteristic value (e.g., amplitude).

In some examples, effective stimulation therapy may rely on a certain level of neural recruitment at a target nerve. This effective stimulation therapy may provide relief from one or more conditions (e.g., patient perceived pain) without an unacceptable level of side effects (e.g., overwhelming perception of stimulation).

Although the system may adjust one or more stimulation parameters according to the one or more characteristics of the sensed ECAP signal, for example, to compensate for the change in distance between electrodes and nerves, the precision of such adjustments is dependent on accurately determining the characteristics of the ECAP signal. For example, noise such as stimulation artifacts and/or linear or exponential background noise may interfere with accurate determinations of the magnitude of one or more peaks within the ECAP signal. Stimulation artifacts typically have amplitudes many times that of the ECAP signal and can at least partially overlap with the ECAPs from nerves. Inaccurate ECAP characterization can reduce the effectiveness of using ECAP characteristic values for automatically adjusting stimulation parameters and result in less efficacious therapy for the patient. Moreover, manually identifying patient thresholds, such as a perception threshold, can be time-consuming and rely on subjective feedback from the patient. Therefore, clinicians may be pressed for time when setting up stimulation, perception thresholds may be inaccurate, and patients may need to return to the clinic in order to update the stimulator programming, for example. These issues may reduce the likelihood that the patient receives efficacious therapy that could otherwise be provided.

As described herein, systems, devices, and techniques are described for analyzing an ECAP signal sensed from the patient in order to determine one or more characteristic values of the ECAP signal, and using the one or more characteristic values of the ECAP signal to estimate a neural threshold for a patient. In one example, the system may attempt to characterize the ECAP signal by removing noise, such as stimulation artifacts, and calculating the absolute value of the difference between two adjacent peaks in the ECAP signal (e.g., between a negative peak and a positive peak, such as the N1 and P2 peaks). Put another way, removal of ECAP signal components associated with stimulation artifacts may increase the accuracy of measuring the difference between the two peaks in the ECAP signal and identifying actual neural recruitment caused by the stimulus. A medical device, such as an implantable medical device, may analyze the more-accurate ECAP signal to determine the one or more characteristic values.

The IMD may utilize the characteristic values of the ECAP signals to determine an estimated neural threshold automatically (e.g., without patient feedback indicating the sensations felt during stimulation). For example, the IMD (or another device, such as an external programmer or other external computing device) may estimate a neural threshold for the patient based on a curve of ECAP characteristic values determined from ECAP signals elicited by respective stimulation pulses of a sweep of pulses defined by different values for one or more stimulation parameter values (e.g., a sweep of pulses having incrementally increasing parameter values such as amplitude). The IMD may determine the estimated neural threshold based on the amplitudes of the curve and a curvature (or width) of the inflection point in the curve associated with increased neural recruitment. This estimated neural threshold may be similar to the perception threshold for the patient. The IMD may use this estimated neural threshold to set initial stimulation amplitudes and/or set one or more thresholds to which subsequent ECAP characteristic values are compared for feedback that informs one or more aspects of electrical stimulation, such as intensity of subsequent electrical stimulation therapy. For example, the IMD may adjust one or more parameter values that defines subsequent electrical stimulation based on the characteristic value and the estimated neural threshold. The IMD may monitor the characteristic values from respective ECAP signals over time and increase or decrease parameter values in order to maintain a target characteristic value or range of values, which may be based on the estimated neural threshold. In another example, the IMD may monitor the characteristic values from ECAP signals over time and reduce a stimulation parameter value when the characteristic value exceeds a threshold in order to reduce the likelihood of overstimulation as perceived by the patient. The IMD may employ these or other control policies based on the determined characteristic value from sensed ECAP signals.

In some examples, the ECAPs detected by an IMD may be ECAPs elicited by stimulation pulses intended to contribute to therapy of a patient or separate pulses (e.g., control pulses) configured to elicit ECAPs that are detectable by the IMD. Nerve impulses detectable as the ECAP signal travel quickly along the nerve fiber after the delivered stimulation pulse first depolarizes the nerve. If the stimulation pulse delivered by first electrodes has a pulse width that is too long, different electrodes configured to sense the ECAP will sense the stimulation pulse itself as an artifact (e.g., detection of delivered charge itself as opposed to detection of a physiological response to the delivered stimulus) that obscures the lower amplitude ECAP signal. However, the ECAP signal loses fidelity as the electrical potentials propagate from the electrical stimulus, because different nerve fibers propagate electrical potentials at different speeds, and fibers in the spine contributing to the ECAP are pruned off. Therefore, sensing the ECAP at a long distance from the stimulating electrodes may help avoid the artifact caused by a stimulation pulse with a long pulse width, but the ECAP signal may be too small or lose fidelity needed to detect changes to the ECAP signal that occur when the electrode-to-target-tissue distance changes. In other words, the system may not be able to identify, at any distance from the stimulation electrodes, ECAPs from stimulation pulses configured to provide a therapy to the patient.

FIG. 1 is a conceptual diagram illustrating an example system 100 that includes an implantable medical device (IMD) 110 configured to deliver spinal cord stimulation (SCS) therapy, and an external programmer 150. Although the techniques described in this disclosure are generally applicable to a variety of medical devices including external devices and IMDs, application of such techniques to IMDs and, more particularly, implantable electrical stimulators (e.g., neurostimulators) will be described for purposes of illustration. More particularly, the disclosure will refer to an implantable SCS system for purposes of illustration, but without limitation as to other types of medical devices or other therapeutic applications of medical devices.

As shown in FIG. 1, system 100 includes IMD 110, leads 130A and 130B, and external programmer 150, shown in conjunction with a patient 105, who is ordinarily a human patient. In the example of FIG. 1, IMD 110 is an implantable electrical stimulator that is configured to generate and deliver electrical stimulation therapy to patient 105 via one or more electrodes of leads 130A and/or 130B (collectively, "leads 130"), e.g., for relief of chronic pain or other symptoms. In other examples, IMD 110 may be coupled to a single lead carrying multiple electrodes or more than two leads each carrying multiple electrodes. In some examples, the stimulation signals, or pulses, may be configured to elicit detectable ECAP signals that IMD 110 may use to determine the posture state occupied by patient 105 and/or determine how to adjust one or more parameters that define stimulation therapy. IMD 110 may be a chronic electrical stimulator that remains implanted within patient 105 for weeks, months, or even years. In other examples, IMD 110 may be a temporary, or trial, stimulator used to screen or evaluate the efficacy of electrical stimulation for chronic therapy. In one example, IMD 110 is implanted within patient 105, while in another example, IMD 110 is an external device coupled to percutaneously implanted leads. In some examples, IMD 110 uses one or more leads, while in other examples, IMD 110 is leadless.

IMD 110 may be constructed of any polymer, metal, or composite material sufficient to house the components of IMD 110 (e.g., components illustrated in FIG. 2) within patient 105. In this example, IMD 110 may be constructed with a biocompatible housing, such as titanium or stainless steel, or a polymeric material such as silicone, polyurethane, or a liquid crystal polymer, and surgically implanted at a site in patient 105 near the pelvis, abdomen, or buttocks. In other examples, IMD 110 may be implanted within other suitable sites within patient 105, which may depend, for example, on the target site within patient 105 for the delivery of electrical stimulation therapy. The outer housing of IMD 110 may be configured to provide a hermetic seal for components, such as a rechargeable or non-rechargeable power source. Additionally or alternatively, the outer housing of IMD 110 may be selected from a material that facilitates receiving energy to charge the rechargeable power source.

Electrical stimulation energy, which may be constant-current or constant-voltage-based pulses, for example, is delivered from IMD 110 to one or more target tissue sites of patient 105 via one or more electrodes (not shown) of implantable leads 130. In the example of FIG. 1, leads 130 carry electrodes that are placed adjacent to the target tissue of spinal cord 120. One or more of the electrodes may be disposed at a distal tip of a lead 130 and/or at other positions at intermediate points along the lead. Leads 130 may be implanted and coupled to IMD 110. The electrodes may transfer electrical stimulation generated by an electrical stimulation generator of IMD 110 to tissue of patient 105. Although leads 130 may each be a single lead, lead 130 may include a lead extension or other segments that may aid in implantation or positioning of lead 130. In some other examples, IMD 110 may be a leadless stimulator with one or more arrays of electrodes arranged on a housing of the stimulator rather than leads that extend from the housing. In some other examples, system 100 may include one lead or more than two leads, each coupled to IMD 110 and directed to similar or different target tissue sites.

The electrodes of leads 130 may be electrode pads on a paddle lead, circular (e.g., ring) electrodes surrounding the body of the lead, conformable electrodes, cuff electrodes, segmented electrodes (e.g., electrodes disposed at different circumferential positions around the lead instead of a continuous ring electrode), any combination thereof (e.g., ring electrodes and segmented electrodes), or any other type of electrodes capable of forming unipolar, bipolar, or multipolar electrode combinations for therapy. Ring electrodes arranged at different axial positions at the distal ends of lead 130 will be described for purposes of illustration.

The deployment of electrodes via leads 130 is described for purposes of illustration, but arrays of electrodes may be deployed in different ways. For example, a housing associated with a leadless stimulator may carry arrays of electrodes, e.g., rows and/or columns (or other patterns), to which shifting operations may be applied. Such electrodes may be arranged as surface electrodes, ring electrodes, or protrusions. As a further alternative, electrode arrays may be formed by rows and/or columns of electrodes on one or more paddle leads. In some examples, electrode arrays include electrode segments, which are arranged at respective positions around a periphery of a lead, e.g., arranged in the form of one or more segmented rings around a circumference of a cylindrical lead. In other examples, one or more of leads 130 are linear leads having eight ring electrodes along the axial length of the lead. In another example, the electrodes are segmented rings arranged in a linear fashion along the axial length of the lead and at the periphery of the lead.

The stimulation parameter set of a therapy stimulation program, which defines the stimulation pulses of electrical stimulation therapy by IMD 110 through the electrodes of leads 130, may include information identifying which electrodes have been selected (e.g., electrode combination) for delivery of stimulation according to a stimulation program, the polarities of the selected electrodes, voltage or current amplitude, pulse frequency, pulse width, and/or a pulse shape of stimulation delivered by the electrodes. These stimulation parameter values may be predetermined parameter values defined by a user and/or automatically determined by system 100 based on one or more factors or user input.

Although FIG. 1 is directed to SCS therapy, e.g., stimulation delivered to the spinal cord and configured to treat pain, in other examples system 100 may be configured to treat any other condition that may benefit from electrical stimulation therapy. For example, system 100 may be used to treat tremor, Parkinson's disease, epilepsy, a pelvic floor disorder (e.g., urinary incontinence or other bladder dysfunction, fecal incontinence, pelvic pain, bowel dysfunction, or sexual dysfunction), obesity, gastroparesis, or psychiatric disorders (e.g., depression, mania, obsessive compulsive disorder, anxiety disorders, and the like). In this manner, system 100 may be configured to provide therapy taking the form of deep brain stimulation (DBS), peripheral nerve stimulation (PNS), peripheral nerve field stimulation (PNFS), cortical stimulation (CS), pelvic floor stimulation, gastrointestinal stimulation, or any other stimulation therapy capable of treating a condition of patient 105.

In some examples, lead 130 includes one or more sensors configured to allow IMD 110 to monitor one or more parameters of patient 105, such as patient activity, pressure, temperature, or other characteristics. The one or more sensors may be provided in addition to, or in place of, therapy delivery by lead 130.

IMD 110 is configured to deliver electrical stimulation therapy to patient 105 via selected combinations of electrodes carried by one or both of leads 130, alone or in combination with an electrode carried by or defined by an outer housing of IMD 110. The target tissue for the electrical stimulation therapy may be any tissue affected by electrical stimulation, which may be in the form of electrical stimulation pulses or continuous waveforms. In some examples, the target tissue includes nerves, smooth muscle, or skeletal muscle. In the example illustrated by FIG. 1, the target tissue is tissue proximate spinal cord 120, such as within an intrathecal space or epidural space of spinal cord 120, or, in some examples, adjacent nerves that branch off spinal cord 120. Leads 130 may be introduced into spinal cord 120 in via any suitable region, such as the thoracic, cervical, or lumbar regions. Stimulation of spinal cord 120 may, for example, prevent pain signals from traveling through spinal cord 120 and to the brain of patient 105. Patient 105 may perceive the interruption of pain signals as a reduction in pain and, therefore, efficacious therapy results. In other examples, stimulation of spinal cord 120 may produce paresthesia, which may reduce the perception of pain by patient 105, and thus, provide efficacious therapy results.

IMD 110 is configured to generate and deliver electrical stimulation therapy to a target stimulation site within patient 105 via the electrodes of leads 130 according to one or more therapy stimulation programs. A therapy stimulation program defines values for one or more parameters (e.g., a parameter set) that define an aspect of the therapy delivered by IMD 110. For example, a therapy stimulation program that controls delivery of stimulation by IMD 110 in the form of pulses may define values for voltage or current pulse amplitude, pulse width, pulse rate (e.g., pulse frequency), electrode combination, pulse shape, etc., for stimulation pulses delivered by IMD 110.

Furthermore, IMD 110 may be configured to deliver stimulation to patient 105 via a combination of electrodes of leads 130, alone or in combination with an electrode carried by or defined by an outer housing of IMD 110, in order to detect ECAP signals. The tissue targeted by the stimulation may be the same or similar tissue targeted by the electrical stimulation therapy, but IMD 110 may deliver stimulation pulses for ECAP signal detection via the same, at least some of the same, or different electrodes.

IMD 110 can deliver stimulation to a target stimulation site within patient 105 via the electrodes of leads 130 according to one or more ECAP stimulation programs to develop a growth curve of the ECAP. The one or more ECAP stimulation programs may be stored in a storage device of IMD 110 and/or external programmer 150. Each ECAP stimulation program of the one or more ECAP stimulation programs includes values for one or more parameters that define an aspect of the stimulation delivered by IMD 110 according to that program, such as current or voltage amplitude, pulse width, pulse frequency, electrode combination, etc. In some examples, the ECAP stimulation program may also define the number of pules and parameter values for each pulse of multiple pulses within a pulse "sweep" configured to obtain a plurality of ECAP signals for respective pulses in order to obtain the growth curve that IMD 110 may use to determine an estimated neural threshold of the patient. In some examples, IMD 110 delivers stimulation to patient 105 according to multiple ECAP stimulation programs. Although these functions are described with respect to IMD 110, other devices, such as external programmer 150, may perform these functions, such as determining the estimated neural threshold based on the growth curve of ECAP characteristic values.

A user, such as a clinician or patient 105, may interact with a user interface of an external programmer 150 to program IMD 110. Programming of IMD 110 may refer generally to the generation and transfer of commands, programs, or other information to control the operation of IMD 110. In this manner, IMD 110 may receive the transferred commands and programs from external programmer 150 to control stimulation, such as electrical stimulation therapy to develop the growth curve. For example, external programmer 150 may transmit therapy stimulation programs, ECAP stimulation programs, stimulation parameter adjustments, therapy stimulation program selections, ECAP program selections, user input, or other information to control the operation of IMD 110, e.g., by wireless telemetry or wired connection.

In some cases, external programmer 150 may be characterized as a "physician programmer" or a "clinician programmer" if it is primarily intended for use by a physician or clinician. In other cases, external programmer 150 may be characterized as a "patient programmer" if it is primarily intended for use by a patient. A patient programmer may be generally accessible to patient 105 and, in many cases, may be a portable device that accompanies patient 105 throughout the patient's daily routine. For example, a patient programmer may receive input from patient 105 when the patient wishes to terminate or change electrical stimulation therapy, when a patient perceives stimulation being delivered or when a patient terminates therapy due to comfort level. In general, a physician or clinician programmer may support selection and generation of programs by a clinician for use by IMD 110, whereas a patient programmer may support adjustment and selection of such programs by a patient during ordinary use. In other examples, external programmer 150 may include, or be part of, an external charging device that recharges a power source of IMD 110. In this manner, a user may program and charge IMD 110 using one device, or multiple devices.

As described herein, information may be transmitted between external programmer 150 and IMD 110. For instance, IMD 110 and external programmer 150 may communicate via wireless communication using any techniques known in the art. Examples of communication techniques may include, for example, radiofrequency (RF) telemetry and inductive coupling, but other techniques are also contemplated. In some examples, external programmer 150 includes a communication head that may be placed proximate to the patient's body near the implant site of IMD 110 in order to improve the quality and/or security of communication between IMD 110 and external programmer 150. Communication between external programmer 150 and IMD 110 may occur during power transmission or separate from power transmission.

In some examples, IMD 110, in response to commands from external programmer 150, delivers electrical stimulation therapy according to a plurality of therapy stimulation programs to a target tissue site of the spinal cord 120 of patient 105 via electrodes (not depicted) on leads 130. In some examples, IMD 110 modifies therapy stimulation programs as therapy needs of patient 105 evolve over time. For example, the modification of the therapy stimulation programs may cause the adjustment of at least one parameter of the plurality of therapy pulses. When patient 105 receives the same therapy for an extended period, the efficacy of the therapy may be reduced. In some cases, parameters of the plurality of therapy pulses may be automatically updated. In some examples, IMD 110 may detect ECAP signals from pulses delivered for the purpose of providing therapy to the patient.

In some examples, efficacy of electrical stimulation therapy may be indicated by one or more characteristics of an action potential that is evoked by a stimulation pulse delivered by IMD 110, for example, by determining an estimated neural response using the characteristic value of the ECAP signal. Electrical stimulation therapy delivery by leads 130 of IMD 110 may cause neurons within the target tissue to evoke a compound action potential that travels up and down the target tissue, eventually arriving at sensing electrodes of IMD 110. Furthermore, stimulation pulses may also elicit at least one ECAP signal, and ECAPs responsive to stimulation may also be a surrogate for the effectiveness of the therapy and/or the intensity perceived by the patient. The amount of action potentials (e.g., number of neurons propagating action potential signals) that are evoked may be based on the various parameters of electrical stimulation pulses such as amplitude, pulse width, frequency, pulse shape (e.g., slew rate at the beginning and/or end of the pulse), etc. The slew rate may define the rate of change of the voltage and/or current amplitude of the pulse at the beginning and/or end of each pulse or each phase within the pulse. For example, a very high slew rate indicates a steep or even near-vertical edge of the pulse, and a low slew rate indicates a longer ramp up (or ramp down) in the amplitude of the pulse. In some examples, these parameters contribute to an intensity of the electrical stimulation. In addition, a characteristic of the ECAP signal (e.g., an amplitude) may change based on the distance between the stimulation electrodes and the nerves subject to the electrical field produced by the delivered control stimulation pulses.

Example techniques for adjusting stimulation parameter values for pulses (e.g., pulses configured to contribute to therapy for the patient) are based on comparing the value of a characteristic of a measured ECAP signal to a target ECAP characteristic value. In some examples, the target ECAP characteristic value may be the estimated neural threshold or a value calculated based on the estimated neural threshold (e.g., a percentage below or above 100% of the estimated neural threshold. During delivery of control stimulation pulses defined by one or more ECAP test stimulation programs, IMD 110, via two or more electrodes interposed on leads 130, senses electrical potentials of tissue of the spinal cord 120 of patient 105 to measure the electrical activity of the tissue. IMD 110 senses ECAPs from the target tissue of patient 105, e.g., with electrodes on one or more leads 130 and associated sensing circuitry. In some examples, IMD 110 receives a signal indicative of the ECAP from one or more sensors, e.g., one or more electrodes and circuitry, internal or external to patient 105. Such a signal may indicate an ECAP of the tissue of patient 105.

In the examples described above, IMD 110 is described as performing a plurality of processing and computing functions. However, external programmer 150 instead may perform one, several, or all of these functions. In this alternative example, IMD 110 relays sensed signals to external programmer 150 for analysis, and external programmer 150 transmits instructions to IMD 110 to adjust the one or more parameters defining the electrical stimulation therapy based on analysis of the sensed signals. For example, IMD 110 may relay the sensed signal indicative of an ECAP to external programmer 150. External programmer 150 may compare the parameter value of the ECAP to the target ECAP characteristic value relative to an estimated neural response, and in response to the comparison, external programmer 150 may instruct IMD 110 to adjust one or more stimulation parameters that define the electrical stimulation pulses delivered to patient 105.

In some examples, the stimulation parameters and the target ECAP characteristic values associated with the estimated neural response may initially be set at the clinic, but may be subsequently set and/or adjusted at home by patient 105. For example, the target ECAP characteristics may be changed to match, or to be a fraction of, or a multiplier of, a stimulation threshold. In some examples, target ECAP characteristics may be specific to respective different posture states of the patient. Once the target ECAP characteristic values are set, the example techniques allow for automatic adjustment of parameter values that define stimulation pulses to maintain a consistent volume of neural activation and consistent perception of therapy for the patient. The ability to change the stimulation parameter values may also allow the therapy to have long-term efficacy, with the ability to keep the intensity of the stimulation (e.g., as indicated by the ECAP) consistent by comparing the measured ECAP values to the target ECAP characteristic value. In addition, or alternatively, to maintaining stimulation intensity, IMD 110 may monitor the characteristic values of the ECAP signals to limit one or more parameter values that define stimulation pulses. IMD 110 may perform these changes without intervention by a physician or patient 105.

In some examples, system 100 changes the target ECAP characteristic value over a period of time, such as according to a change to a stimulation threshold (e.g., a perception threshold or detection threshold). The system may be programmed to change the target ECAP characteristic in order to adjust the intensity of stimulation pulses to provide varying sensations to the patient (e.g., increase or decrease the volume of neural activation). Although the system may change the target ECAP characteristic value, received ECAP signals may still be used by the system to adjust one or more parameter values of the stimulation pulse in order to meet the target ECAP characteristic value.

One or more devices within system 100, such as IMD 110 and/or external programmer 150, may perform various functions as described herein. For example, IMD 110 may include stimulation circuitry configured to deliver electrical stimulation, sensing circuitry configured to sense a plurality ECAP signals, and processing circuitry. The processing circuitry may be configured to control the stimulation circuitry to deliver a plurality of electrical stimulation pulses having different amplitude values and control the sensing circuitry to detect, after delivery of each electrical stimulation pulse, a respective ECAP signal, and to determine ECAP characteristic values for each of the ECAP signals. The processing circuitry of IMD 110 may then determine, based on the plurality of ECAP characteristic values, an estimated neural threshold of a patient. The estimated neural threshold may be similar to a perception threshold that the patient would have manually identified during the sweep of increasing amplitude values of stimulation. As such, IMD 110, or another device such as external programmer 150, may automatically determine the estimated neural threshold, e.g., without patient input.

In some examples, IMD 110 may include the stimulation circuitry, the sensing circuitry, and the processing circuitry. However, in other examples, one or more additional devices may be part of the system that performs the functions described herein. For example, IMD 110 may include the stimulation circuitry and the sensing circuitry, but external programmer 150 or another external device may include the processing circuitry that at least determines the estimated neural threshold of the patient. IMD 110 may transmit the sensed ECAP signals, or data representing the ECAP signal, to external programmer 150, for example. Therefore, the processes described herein may be performed by multiple devices in a distributed system. In some examples, system 100 may include one or more electrodes that deliver and/or sense electrical signals. Such electrodes may be configured to sense the ECAP signals. In some examples, the same electrodes may be configured to sense signals representative of transient movements of the patient. In other examples, other sensors, such as accelerometers, gyroscopes, or other movement sensors may be configured to sense movement of the patient that indicates that the patient may have transitioned to a different posture state.

As described herein, the processing circuitry of IMD 110 may be configured to determine characteristic values for each of the plurality of ECAP signals detected after each of the plurality of electrical stimulation pulses. A plurality of stimulation pulses is delivered, where each stimulation pulse may be defined by a different respective value of a stimulation parameter. The plurality of stimulation pulses may include increasing amplitudes to elicit different responses of ECAP signal information. In one or more examples, the characteristic value for each ECAP signal is a representation of the ECAP signal according to some metric, and is determined by IMD 110, for example, by removing an artifact from the ECAP signal. These characteristic values may thus be used as a metric derived from the ECAP signal that represents the relative nerve fiber activation caused by the delivered stimulation pulse. In this manner, each ECAP signal is associated with a respective characteristic value of the characteristic values. As long as the distance between the electrodes and target nerve remains relatively constant during delivery of the pulses and sensing of the respective ECAP signals, higher amplitude pulses generally cause more neural recruitment and larger ECAP signals.

As described herein, the processing circuitry of IMD 110 may be configured to determine an estimated neural threshold of a patient based on characteristic values for the plurality of ECAP signals detected after each of the plurality of electrical stimulation pulses. For example, the estimated neural threshold may be determined by sweeping through a plurality of amplitudes for respective stimulation pulses and generating a growth curve from the sensed ECAP signals. The growth curve may be used to determine an estimated neural threshold, for example, when the growth curve transitions from a first linear region to a second curvilinear region. In some examples, the system may determine a therapeutic range based on one or more characteristics of the second curvilinear region (e.g., radius of curvature, width of current amplitude of the curvilinear region, ratio of ECAP amplitude width and current amplitude width of the curvilinear region, etc.). In this manner, as further described herein, the system may use this sweep of pulses, or as part of additional sweeps of pulses varying one or more parameter values, to automatically determine parameter values for therapy based on ECAP characteristic(s). The sweep of amplitudes for stimulation pulses may be linear, non-linear, or even adaptive based on sensed information. In one or more examples, the IMD (or external programmer) may step through the first linear region by increasing a value of one or more of the plurality of stimulation parameters in greater steps (e.g., a faster rate of change), and once an inflection in the curve is sensed, the system may reduce the rate of change for stimulation amplitude to slow the stepping of changes (i.e., adaptive stepping). In one or more examples, the processing circuitry may increase the value of the stimulation parameter until the estimated neural threshold is determined or can be determined, and then stop delivering stimulation for the sweep. In other examples, the system may continue performing the sweep of amplitudes until a predetermined amplitude value is reached or the system receives input from the patient requesting that stimulation be stopped (e.g., the patient has reached a discomfort threshold). If input from the patient indicates that the discomfort threshold has been reached, the system may set the discomfort threshold stimulation amplitude as the upper threshold for stimulation during therapy.

In one example, system 100 (which may be or may include IMD 110, external programmer 150, and/or off-site or networked computing systems) may include a stimulation generator configured to deliver a stimulation pulse to patient 105, and sensing circuitry configured to sense an ECAP signal evoked by the stimulation pulse. System 100 may also include processing circuitry configured to determine ECAP characteristic values for each of the ECAP signals, and determine a targeted range of ECAP characteristic values based on the growth curve that is based on the estimated neural response, which may be a range, a characteristic value of the targeted ECAP signal, and at least one parameter value at least partially defining electrical stimulation therapy to be delivered or offered to the patient. The patient or clinician may further modify the stimulation therapy, for example, based on patient preference or expected battery life, for example.

In one example, IMD 110 may determine a target ECAP characteristic value based on the estimated neural response, and calculate the at least one parameter value according to a difference between the current ECAP characteristic value. In this manner, IMD 110 may deliver stimulation in closed-loop fashion using ECAP characteristic values as feedback. Processing circuitry of IMD 110 may thus be configured to control the stimulation generator to deliver the electrical stimulation therapy to the patient according to the at least one adjusted parameter value, which may be selected based on the ECAP characteristic values and/or estimated neural threshold. IMD 110 may include stimulation circuitry, sensing circuitry, and processing circuitry. In some examples, other devices, such as an external device or different implanted device, may analyze ECAP signals for characteristic values and/or adjust parameter values that define stimulation pulses based on the characteristic values.

Although in the example of FIG. 1, IMD 110 takes the form of an SCS device, in other examples, IMD 110 takes the form of any combination of deep brain stimulation (DBS) devices, peripheral nerve stimulators, implantable cardioverter defibrillators (ICDs), pacemakers, cardiac resynchronization therapy devices (CRT-Ds), left ventricular assist devices (LVADs), implantable sensors, orthopedic devices, or drug pumps, as examples. Moreover, techniques of this disclosure may be used to determine stimulation thresholds (e.g., perception thresholds and detection thresholds) associated any one of the aforementioned IMDs and then use a stimulation threshold to inform the intensity (e.g., stimulation levels) of therapy.

Figure 2:
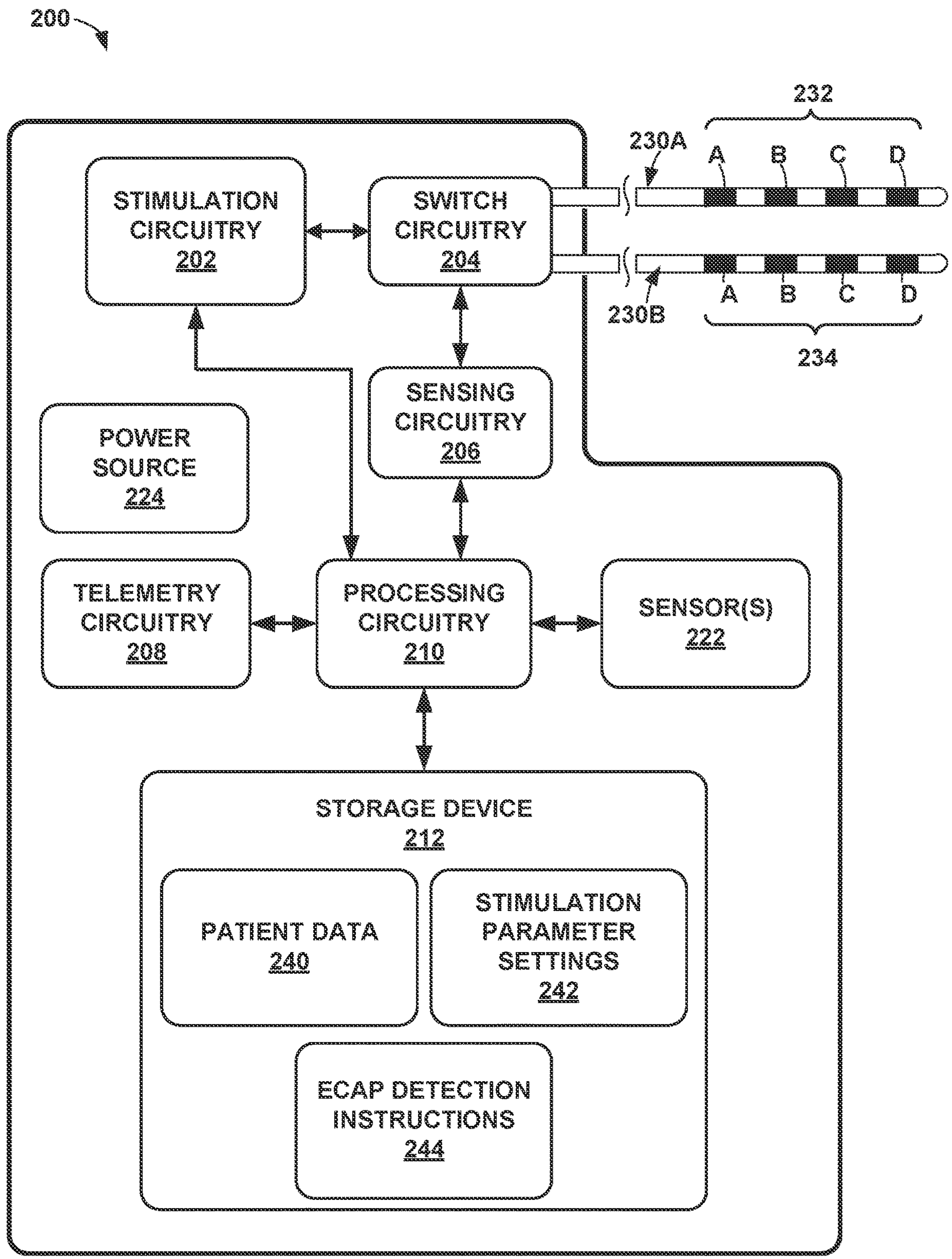
FIG. 2 is a block diagram illustrating an example configuration of components of the IMD of FIG. 1.

FIG. 2 is a block diagram illustrating an example configuration of components of an IMD 200. IMD 200 may be an example of IMD 110 of FIG. 1. In the example shown in FIG. 2, IMD 200 includes stimulation generation circuitry 202, switch circuitry 204, sensing circuitry 206, telemetry circuitry 208, processing circuitry 210, storage device 212, sensor(s) 222, and power source 224.

In the example shown in FIG. 2, storage device 212 stores patient data 240, stimulation parameter settings 242, and ECAP detection instructions 244 in separate memories within storage device 212 or separate areas within storage device 212. Patient data 240 may include parameter values, target characteristic values, or other information specific to the patient. In some examples, stimulation parameter settings 242 may include stimulation parameter values for respective different stimulation programs selectable by the clinician or patient for therapy. In this manner, each stored therapy stimulation program, or set of stimulation parameter values, of stimulation parameter settings 242 defines values for a set of electrical stimulation parameters (e.g., a stimulation parameter set), such as a stimulation electrode combination, electrode polarity, current or voltage amplitude, pulse width, pulse rate, pulse shape, and/or duty cycle. Storage device 212 may also store ECAP detection instructions 244 that define values for a set of electrical stimulation parameters configured to elicit a detectable ECAP signal, such as a stimulation electrode combination, electrode polarity, current or voltage amplitude, pulse width, pulse rate, and/or pulse shape. ECAP detection instructions 244 may also have additional information such as instructions regarding when to deliver control pulses based on the pulse width and/or frequency of the pulses defined in stimulation parameter settings 242, detection windows for detecting ECAP signals, instructions for determining characteristic values from ECAP signals, etc. For example, ECAP detection instructions 244 may define how characteristic values of ECAP signals are to be determined.

Accordingly, in some examples, stimulation generation circuitry 202 generates electrical stimulation signals in accordance with the electrical stimulation parameters noted above. Other ranges of stimulation parameter values may also be useful and may depend on the target stimulation site within patient 105. While stimulation "pulses" are primarily described herein, stimulation signals may be of any form, such as continuous-time signals (e.g., sine waves) or the like.

Switch circuitry 204 may include one or more switch arrays, one or more multiplexers, one or more switches (e.g., a switch matrix or other collection of switches), or other electrical circuitry configured to direct stimulation signals from stimulation generation circuitry 202 to one or more of electrodes 232, 234, or direct sensed signals from one or more of electrodes 232, 234 to sensing circuitry 206. In other examples, stimulation generation circuitry 202 and/or sensing circuitry 206 may direct signals to and/or from one or more of electrodes 232, 234, which may or may not also include switch circuitry 204.

Sensing circuitry 206 is configured to monitor signals from any combination of electrodes 232, 234. In some examples, sensing circuitry 206 includes one or more amplifiers, filters, and/or analog-to-digital converters. Sensing circuitry 206 may be used to sense physiological signals, such as ECAP signals. In some examples, sensing circuitry 206 detects ECAPs from a particular combination of electrodes 232, 234. In some cases, the particular combination of electrodes for sensing ECAPs includes different electrodes than a set of electrodes 232, 234 used to deliver stimulation pulses. Alternatively, in other cases, the particular combination of electrodes used for sensing ECAPs includes at least one of the same electrodes as a set of electrodes used to deliver stimulation pulses to patient 105. Sensing circuitry 206 may provide signals to an analog-to-digital converter for conversion into a digital signal for processing, analysis, storage, and/or output by processing circuitry 210.

Telemetry circuitry 208 supports wireless communication between IMD 200 and an external programmer (not shown in FIG. 2) or another computing device under the control of processing circuitry 210. Processing circuitry 210 of IMD 200 may receive, as updates to programs, values for various stimulation parameters (e.g., amplitude and electrode combination) from the external programmer via telemetry circuitry 208. Processing circuitry 210 may store updates to the stimulation parameter settings 242 or any other data in storage device 212. Telemetry circuitry 208 in IMD 200, as well as telemetry circuits in other devices and systems described herein, such as the external programmer, may accomplish communication by radiofrequency (RF) communication techniques. In addition, telemetry circuitry 208 may communicate with an external medical device programmer (not shown in FIG. 2) via proximal inductive interaction of IMD 200 with the external programmer. The external programmer may be one example of external programmer 150 of FIG. 1. Accordingly, telemetry circuitry 208 may send information to the external programmer on a continuous basis, at periodic intervals, or upon request from IMD 110 or the external programmer.

Processing circuitry 210 may include any one or more of a microprocessor, a controller, a digital signal processor (DSP), an application specific integrated circuit (ASIC), a field-programmable gate array (FPGA), discrete logic circuitry, or any other processing circuitry configured to provide the functions attributed to processing circuitry 210 herein may be embodied as firmware, hardware, software or any combination thereof. Processing circuitry 210 controls stimulation generation circuitry 202 to generate stimulation signals according to stimulation parameter settings 242 and any other instructions stored in storage device 212 to apply stimulation parameter values specified by one or more of programs, such as amplitude, pulse width, pulse rate, and pulse shape of each of the stimulation signals.

In the example shown in FIG. 2, the set of electrodes 232 includes electrodes 232A, 232B, 232C, and 232D, and the set of electrodes 234 includes electrodes 234A, 234B, 234C, and 234D. In other examples, a single lead may include all eight electrodes 232 and 234 along a single axial length of the lead. Processing circuitry 210 also controls stimulation generation circuitry 202 to generate and apply the stimulation signals to selected combinations of electrodes 232, 234. In some examples, stimulation generation circuitry 202 includes a switch circuit (instead of, or in addition to, switch circuitry 204) that may couple stimulation signals to selected conductors within leads 230, which, in turn, deliver the stimulation signals across selected electrodes 232, 234. Such a switch circuit may be a switch array, switch matrix, multiplexer, or any other type of switching circuit configured to selectively couple stimulation energy to selected electrodes 232, 234 and to selectively sense bioelectrical neural signals of a spinal cord of the patient (not shown in FIG. 2) with selected electrodes 232, 234.

In other examples, however, stimulation generation circuitry 202 does not include a switch circuit and switch circuitry 204 does not interface between stimulation generation circuitry 202 and electrodes 232, 234. In these examples, stimulation generation circuitry 202 includes a plurality of pairs of voltage sources, current sources, voltage sinks, or current sinks connected to each of electrodes 232, 234 such that each pair of electrodes has a unique signal circuit. In other words, in these examples, each of electrodes 232, 234 is independently controlled via its own signal circuit (e.g., via a combination of a regulated voltage source and sink or regulated current source and sink), as opposed to switching signals between electrodes 232, 234.

Electrodes 232, 234 on respective leads 230 may be constructed of a variety of different designs. For example, one or both of leads 230 may include one or more electrodes at each longitudinal location along the length of the lead, such as one electrode at different perimeter locations around the perimeter of the lead at each of the locations A, B, C, and D. In one example, the electrodes may be electrically coupled to stimulation generation circuitry 202, e.g., via switch circuitry 204 and/or switching circuitry of the stimulation generation circuitry 202, via respective wires that are straight or coiled within the housing of the lead and run to a connector at the proximal end of the lead. In another example, each of the electrodes of the lead may be electrodes deposited on a thin film. The thin film may include an electrically conductive trace for each electrode that runs the length of the thin film to a proximal end connector. The thin film may then be wrapped (e.g., a helical wrap) around an internal member to form the lead 230. These and other constructions may be used to create a lead with a complex electrode geometry.

Although sensing circuitry 206 is incorporated into a common housing with stimulation generation circuitry 202 and processing circuitry 210 in FIG. 2, in other examples, sensing circuitry 206 may be in a separate housing from IMD 200 and may communicate with processing circuitry 210 via wired or wireless communication techniques. In some examples, one or more of electrodes 232 and 234 are suitable for sensing the ECAPs. For instance, electrodes 232 and 234 may sense the voltage amplitude of a portion of the ECAP signals, where the sensed voltage amplitude, such as the voltage difference between features within the signal, is a characteristic the ECAP signal.

Storage device 212 may be configured to store information within IMD 200 during operation. Storage device 212 may include a computer-readable storage medium or computer-readable storage device. In some examples, storage device 212 includes one or more of a short-term memory or a long-term memory. Storage device 212 may include, for example, random access memories (RAM), dynamic random access memories (DRAM), static random access memories (SRAM), magnetic discs, optical discs, flash memories, or forms of electrically programmable memories (EPROM) or electrically erasable and programmable memories (EEPROM). In some examples, storage device 212 is used to store data indicative of instructions for execution by processing circuitry 210. As discussed above, storage device 212 is configured to store patient data 240, stimulation parameter settings 242, and ECAP detection instructions 244.

In some examples, storage device 212 may store instructions on how processing circuitry 210 can adjust stimulation pulses in response to the determined characteristic values of ECAP signals. For example, processing circuitry 210 may monitor ECAP characteristic values obtained from ECAP signals (or a signal derived from the ECAP signal) to modulate stimulation parameter values (e.g., increase or decrease stimulation intensity to maintain a target therapeutic effect). In some examples, a target ECAP characteristic value may vary for different situations for a patient, such as different posture states, times of day, activities, etc.

Sensor(s) 222 may include one or more sensing elements that sense values of a respective patient parameter, such as posture state. As described, electrodes 232 and 234 may be the electrodes that sense the characteristic value of the ECAP signal. Sensor(s) 222 may include one or more accelerometers, optical sensors, chemical sensors, temperature sensors, pressure sensors, or any other types of sensors. Sensor(s) 222 may output patient parameter values that may be used as feedback to control delivery of therapy. For example, sensor(s) 222 may indicate patient activity, and processing circuitry 210 may increase the frequency of control pulses and ECAP sensing in response to detecting increased patient activity. In one example, processing circuitry 210 may initiate control pulses and corresponding ECAP sensing in response to a signal from sensor(s) 222 indicating that patient activity has exceeded an activity threshold. Conversely, processing circuitry 210 may decrease the frequency of control pulses and ECAP sensing in response to detecting decreased patient activity. For example, in response to sensor(s) 222 no longer indicating that the sensed patient activity exceeds a threshold, processing circuitry 210 may suspend or stop delivery of control pulses and ECAP sensing. In this manner, processing circuitry 210 may dynamically deliver control pulses and sense ECAP signals based on patient activity to reduce power consumption of the system when the electrode-to-neuron distance is not likely to change, and may increase a system response to ECAP changes when electrode-to-neuron distance is likely to change. IMD 200 may include additional sensors within the housing of IMD 200 and/or coupled via one of leads 130 or other leads. In addition, IMD 200 may receive sensor signals wirelessly from remote sensors via telemetry circuitry 208, for example. In some examples, one or more of these remote sensors may be external to patient (e.g., carried on the external surface of the skin, attached to clothing, or otherwise positioned external to patient 105). In some examples, signals from sensor(s) 222 indicate a position or body state (e.g., sleeping, awake, sitting, standing, or the like), and processing circuitry 210 may select target ECAP characteristic values according to the indicated position or body state.

Power source 224 is configured to deliver operating power to the components of IMD 200. Power source 224 may include a battery and a power generation circuit to produce the operating power. In some examples, the battery is rechargeable to allow extended operation. In some examples, recharging is accomplished through proximal inductive interaction between an external charger and an inductive charging coil within IMD 200. Power source 224 may include any one or more of a plurality of different battery types, such as nickel cadmium batteries and lithium ion batteries.

Figure 3:
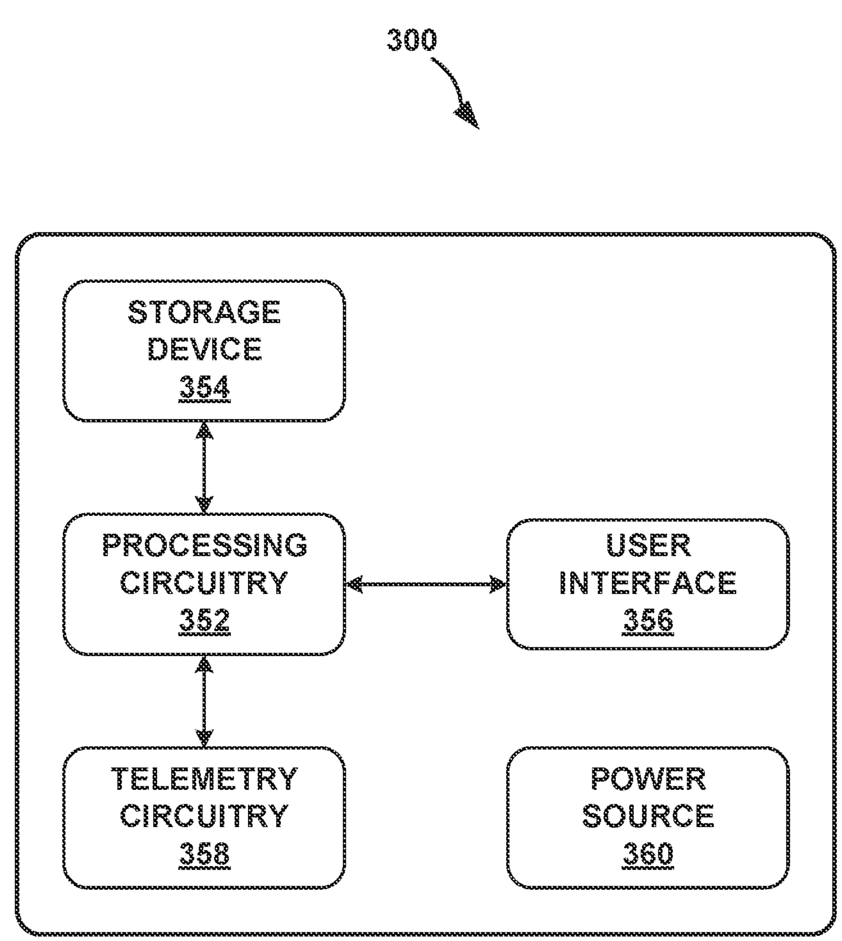
FIG. 3 is a block diagram illustrating an example configuration of components of an example external programmer.

FIG. 3 is a block diagram illustrating an example configuration of components of an example external programmer 300. External programmer 300 may be an example of external programmer 150 of FIG. 1. Although external programmer 300 may generally be described as a handheld device, external programmer 300 may be a larger portable device or a more stationary device. In other examples, external programmer 300 may be included as part of an external charging device or may include the functionality of an external charging device. As illustrated in FIG. 3, external programmer 300 may include processing circuitry 352, storage device 354, user interface 356, telemetry circuitry 358, and power source 360.

Storage device 354 may store instructions that, when executed by processing circuitry 352, cause processing circuitry 352 and external programmer 300 to provide the functionality ascribed to external programmers 150, 300 throughout this disclosure. Each of these components, circuitry, or modules may include electrical circuitry that is configured to perform some, or all of the functionality described herein. For example, processing circuitry 352 may include processing circuitry configured to perform the processes discussed with respect to processing circuitry 352.

In general, external programmer 300 includes any suitable arrangement of hardware, alone or in combination with software and/or firmware, to perform the techniques attributed to external programmer 300, and processing circuitry 352, user interface 356, and telemetry circuitry 358 of external programmer 300. In various examples, external programmer 300 may include one or more processors, such as one or more microprocessors, DSPs, ASICs, FPGAs, or any other equivalent integrated or discrete logic circuitry, as well as any combinations of such components. External programmer 300 also, in various examples, may include a storage device 354, such as RAM, ROM, PROM, EPROM, EEPROM, flash memory, a hard disk, a CD-ROM, including executable instructions for causing the one or more processors to perform the actions attributed to them. Moreover, although processing circuitry 352 and telemetry circuitry 358 are described as separate modules, in some examples, processing circuitry 352 and telemetry circuitry 358 are functionally integrated. In some examples, processing circuitry 352 and telemetry circuitry 358 correspond to individual hardware units, such as ASICs, DSPs, FPGAS, or other hardware units.

Storage device 354 (e.g., a memory or other device configured to store data) may store instructions that, when executed by processing circuitry 352, cause processing circuitry 352 and external programmer 300 to provide the functionality ascribed to external programmers 150, 300 throughout this disclosure. For example, storage device 354 may include instructions that cause processing circuitry 352 to obtain a parameter set from memory, select a spatial electrode pattern, receive a user input and send a corresponding command to IMD 200, or any other functionality. Storage device 354 may include a plurality of programs, where each program includes a parameter set that defines therapy stimulation or control stimulation. Storage device 354 may also store data received from a medical device (e.g., IMD 110). For example, storage device 354 may store ECAP-related data recorded at a sensing module of the medical device, and storage device 354 may also store data from one or more sensors of the medical device.

User interface 356 may include a button or keypad, lights, a speaker for voice commands, a display, such as a liquid crystal display (LCD), light-emitting diode (LED), or organic light-emitting diode (OLED). In some examples the display includes a touchscreen. User interface 356 may be configured to display any information related to the delivery of electrical stimulation, identified posture states, sensed patient parameter values, or any other such information. User interface 356 may also receive user input (e.g., indication of when the patient perceives a stimulation pulse) via user interface 356. The input may be, for example, in the form of pressing a button on a keypad or selecting an icon from a touchscreen. The input may request starting or stopping electrical stimulation, a new spatial electrode pattern or a change to an existing spatial electrode pattern, or some other change to the delivery of electrical stimulation.

Telemetry circuitry 358 may support wireless communication between the medical device and external programmer 300 under the control of processing circuitry 352. Telemetry circuitry 358 may also be configured to communicate with another computing device via wireless communication techniques, or direct communication through a wired connection. In some examples, telemetry circuitry 358 provides wireless communication via an RF or proximal inductive medium. In some examples, telemetry circuitry 358 includes an antenna, which may take on a variety of forms, such as an internal or external antenna.

Examples of local wireless communication techniques that may be employed to facilitate communication between external programmer 300 and IMD 110 include RF communication according to the 802.11 or Bluetooth® specification sets or other standard or proprietary telemetry protocols. In this manner, other external devices may be capable of communicating with external programmer 300 without needing to establish a secure wireless connection. As described herein, telemetry circuitry 358 may be configured to transmit a spatial electrode movement pattern or other stimulation parameter values to IMD 110 for delivery of electrical stimulation therapy. Although IMD 110 may determine characteristic values for ECAP signals and control the adjustment of stimulation parameter values in some examples, programmer 300 may perform these tasks alone or together with IMD 110 in a distributed function.

In some examples, selection of stimulation parameters or therapy stimulation programs are transmitted to the medical device for delivery to a patient (e.g., patient 105 of FIG. 1). In other examples, the therapy may include medication, activities, or other instructions that patient 105 must perform themself or a caregiver perform for patient 105. In some examples, external programmer 300 provides visual, audible, and/or tactile notifications that indicate there are new instructions. External programmer 300 requires receiving user input acknowledging that the instructions have been completed in some examples.

User interface 356 of external programmer 300 may also be configured to receive an indication from a clinician instructing a processor of the medical device to update one or more therapy stimulation programs or to update the target characteristic values for ECAP signals. Updating therapy stimulation programs and target characteristic values may include changing one or more parameters of the stimulation pulses delivered by the medical device according to the programs, such as amplitude, pulse width, frequency, and/or pulse shape of the therapy pulses and/or control pulses. User interface 356 may also receive instructions from the clinician commanding any electrical stimulation, including therapy stimulation and control stimulation, to commence or to cease.

Power source 360 is configured to deliver operating power to the components of external programmer 300. Power source 360 may include a battery and a power generation circuit to produce the operating power. In some examples, the battery is rechargeable to allow extended operation. Recharging may be accomplished by electrically coupling power source 360 to a cradle or plug that is connected to an alternating current (AC) outlet. In addition, recharging may be accomplished through proximal inductive interaction between an external charger and an inductive charging coil within external programmer 300. In other examples, traditional batteries (e.g., nickel cadmium or lithium ion batteries) may be used. In addition, external programmer 300 may be directly coupled to an alternating current outlet to operate.

The architecture of external programmer 300 illustrated in FIG. 3 is shown as an example. The techniques as set forth in this disclosure may be implemented in the example external programmer 300 of FIG. 3, as well as other types of systems not described specifically herein. Nothing in this disclosure should be construed so as to limit the techniques of this disclosure to the example architecture illustrated by FIG. 3.

Figure 4A:
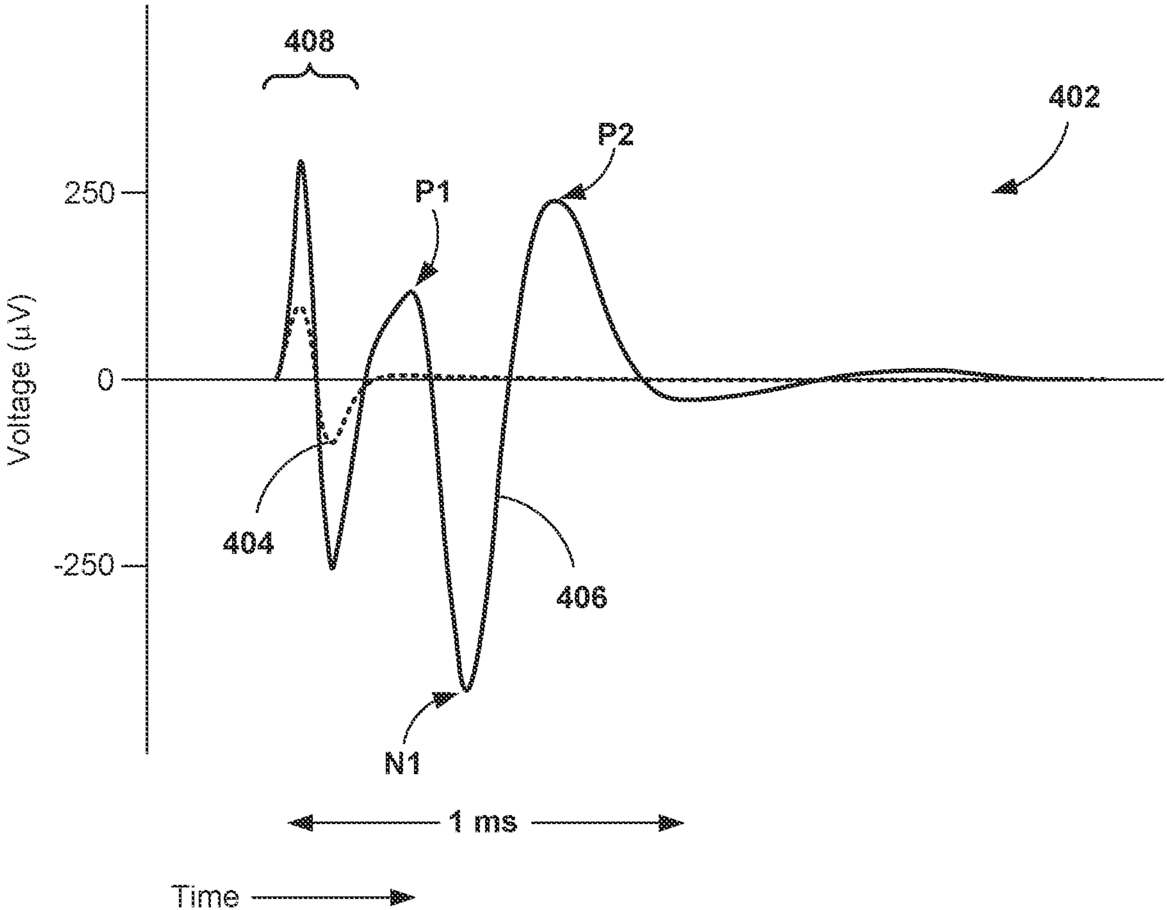
FIG. 4A is a graph of example evoked compound action potentials (ECAPs) sensed for respective stimulation pulses.

FIG. 4A is a graph 402 of example evoked compound action potentials (ECAPs) sensed for respective stimulation pulses, in accordance with one or more techniques of this disclosure. As shown in FIG. 4A, graph 402 shows example ECAP signal 404 (dotted line) and ECAP signal 406 (solid line). In some examples, each of ECAP signals 404 and 406 are sensed from stimulation pulses that were delivered from a guarded cathode, where the control pulses are bi-phasic pulses including an interphase interval between each positive and negative phase of the pulse. In some such examples, the guarded cathode includes stimulation electrodes located at the end of an 8-electrode lead (e.g., leads 130 of FIG. 1) while two sensing electrodes are provided at the other end of the 8-electrode lead. ECAP signal 404 illustrates the voltage amplitude sensed as a result from a sub-detection threshold stimulation pulse. In other words, the stimulation pulse did not elicit a detectable ECAP signal in ECAP signal 404. Peaks 408 of ECAP signal 404 are detected and represent the artifact of the delivered stimulation pulse (e.g., a control pulse that may or may not contribute to a therapeutic effect for the patient). However, no propagating signal is detected after the artifact in ECAP signal 404 because the stimulation pulse was sub-detection threshold (e.g., the intensity of the stimulation pulse was insufficient to cause nerve fibers to depolarize and generate a detectable ECAP signal).

In contrast to ECAP signal 404, ECAP signal 406 represents the voltage amplitude detected from a supra-detection threshold stimulation pulse. Peaks 408 of ECAP signal 406 are detected and represent the artifact of the delivered stimulation pulse. After peaks 408, ECAP signal 406 also includes peaks P1, N1, and P2, which are three typical peaks representative of propagating action potentials from an ECAP. The example duration of the artifact and peaks P1, N1, and P2 is approximately 1 millisecond (ms). The time between two points in the ECAP signal may be referred to as a "latency" of the ECAP and may indicate the types of fibers being captured by the control pulse. ECAP signals with lower latency (i.e., smaller latency values) indicate a higher percentage of nerve fibers that have faster propagation of signals, whereas ECAP signals with higher latency (i.e., larger latency values) indicate a higher percentage of nerve fibers that have slower propagation of signals. Other characteristics of the ECAP signal may be used in other examples.

The amplitude of the ECAP signal (e.g., of peaks within the ECAP signal) generally increases with increased amplitude of the stimulation pulse, as long as the pulse amplitude is greater than the threshold such that nerves depolarize and propagate the signal. The target ECAP characteristic (e.g., the target ECAP amplitude) may be determined from an ECAP signal associated with an estimated neural response detected from pulses delivering therapy to patient 105 (FIG. 1). The ECAP signal thus is representative of the distance between the stimulation electrodes and the nerves appropriate for the stimulation parameter values of the pulses delivered at that time.

In some examples, processing circuitry 210 (FIG. 2) or other devices may be configured to determine a characteristic value for an ECAP signal, for example, from multiple different features of one or more signals associated with the ECAP signal. The characteristic value of the ECAP signal may be determined by removing an artifact from the ECAP signal using the processing circuitry. These different features may be incorporated into an average, weighted average, or other combination that represents the relative action potentials of the ECAP signal. Processing circuitry 210 may determine the characteristic value from different features of the same signal, such as the amplitude difference between two peaks in the ECAP signal and the amplitude difference between two different peaks in the ECAP signal. As another example of features from the same signal, processing circuitry 210 may determine the characteristic value based on an average of two different peaks in the second derivative signal. Alternatively, processing circuitry 210 may determine the characteristic value of the ECAP signal from features obtained from different signals. For example, processing circuitry 210 may determine the difference between the minimum and maximum values of the first derivative of the ECAP signal on either side of the P2 peak, determine the maximum value of the second derivative of the ECAP signal, and combine each of these factors into a single characteristic value of the ECAP signal. This single characteristic value of the ECAP signal may be referred to as a "composite" characteristic value because it is a composite of several different factors derived from the ECAP signal in order to obtain a more complete representation of the ECAP signal.

In one or more examples, the ECAP characteristic values may be determined after subtracting the artifact, to the extent an artifact may be present during some portion of the sensed ECAP signal. In some examples, that artifact may be modeled as a sum of exponential and a linear component. In another example, the artifact may be modeled sufficiently by either an exponential or a linear component alone. In order to fit the artifact to the response for the growth curve, several methods may be used. In one or more examples, the method may include estimating a minimum in the error function between the artifact model and the measured response. For example, if parameters of the function are P (e.g., time constant of the exponential, gain and linear slope and offset), the error function may be:

$$Err(P)=E[E(t)-A(P,t)]$$

The optimal fit is to find $P_{opt}$ where the error Err(P) is minimized. The ECAP characteristic value may be determined the recording E(t) as:

$$ECAP(t)=E(t)-A(P_{opt},t)$$

A common error function Err is something like a norm-2, which is defined as $$E=sqrt\left[\text{sum\_t}\left((E(t)-A(P,t))^2\right]\right.$$

An example model A(P, t) with four parameters is as follows:

$$A(P,t)=\exp\left(-t/P(1)\right)*P(2)+t*P(3)+P(4)$$

In one or more examples, the error function may be modified by a weight function W(t), where W(t) is high for instances where the neural response is low, for example, in the first region. For example, the W function may be high for t early in the measured waveform E(t) (e.g., prior to neural response developing), and low where the neural response can be high. In some examples, W(t) can be higher after the response.

$$E[P]=sqrt\left(\text{sum\_t}\left(W(t)*(E(t)-A(P,t))^2\right)\right.$$

In this way, the model can be fit more specifically to the artifact, and not to the neural response, for example, for the first region. The weight can thus be adjusted by the system to reduce the effect of any stimulation artifact while maintaining the desired ECAP components of the signal. Note that, for this analysis, a uniform weight W may be used, so this feature may be optional.

It is also understood that, once the time constant P(1) is estimated, the rest of the parameters may be solved. For instance, in some examples, if M is defined as a matrix with rows [exp(−t/P(1))t1] and $W_m$ is a matrix with diagonal equal to W, then parameters P(2) to P(4) may be:

$$P_{end}=(A'*\text{diag}(W')*\text{diag}(W)*A)\backslash(A'*\text{diag}(W')*\text{diag}(W)*\text{data})$$

Figure 4B:
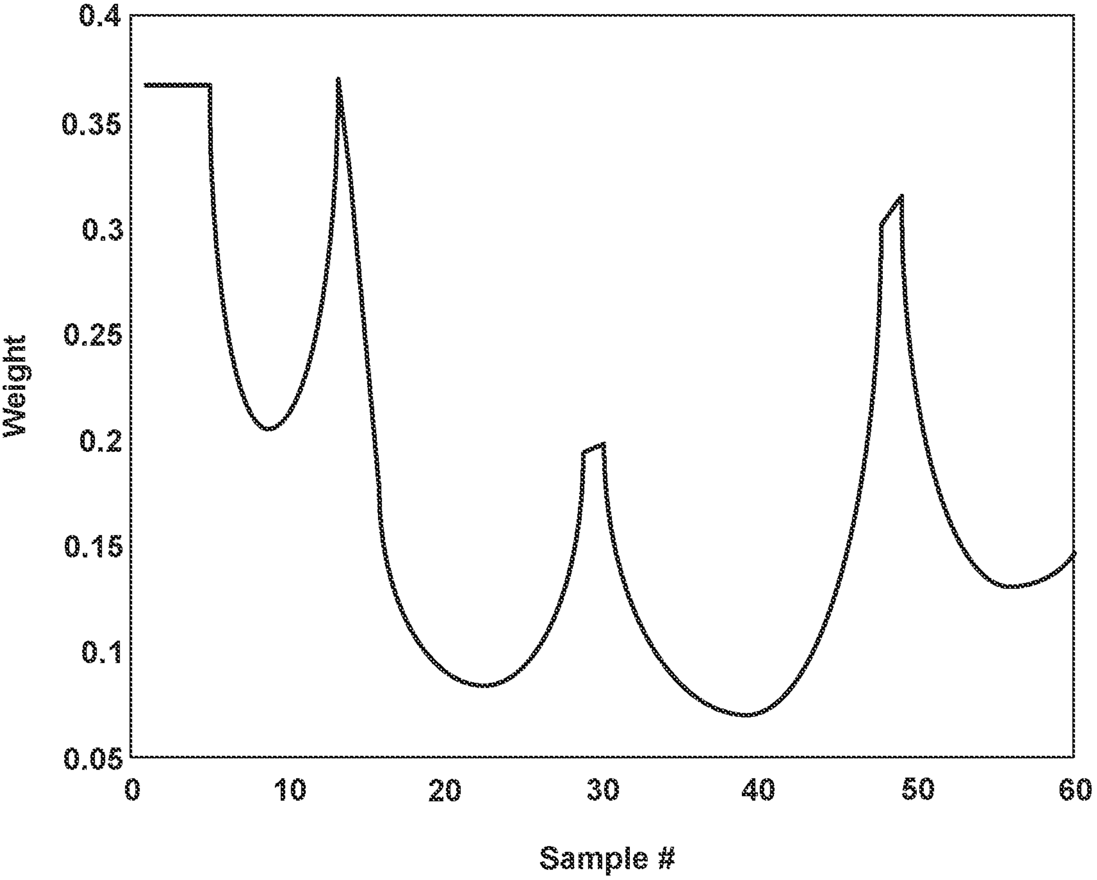
FIG. 4B is a graph of an example weight array W for multiple samples.

In the above table, the "\" operator is a matrix inversion operator and diag(W) transforms the weight vector of length n to a matrix of weight n with contents of W. An example weight array W is shown in FIG. 4B. Features of interest in W may include high starting level (where most of the artifact is contained but ECAP response is low), and low weight for features which may contain the main ECAP energy (e.g. around samples 20 and 40). In addition, weight W might contain peaks corresponding to typical transition regions (e.g. peak around sample 11 or sample 30).

For real-time systems, the matrix multiplication operation may be fairly efficient. Thus, there may be an adaptive procedure to solve for P(1) (for example by back-propagation of error method) and then an analytic method to solve for P(2) to P(4). In one or more examples, if the artifact can change fairly rapidly, the speed of the back-propagation type of algorithm may be adjusted depending on the error term (e.g., large errors can lead to faster adaptation of P(1)). In some examples, either P(1) or range of P(1) can be estimated using equipment external to the implant, such as a clinician programmer or a patient programmer.

For certain weight functions, the equation for Pend can be a sparse equation and can be reduced to a non-FIR filter model. In addition, several P(1) candidates may be evaluated and the smallest one can be selected for the algorithm. Another alternative may be to determine evaluate several P(1) candidates and to pick the minimum one, but to utilize the adjacent near-by measurements to fit a curve, e.g. a parabola, to more precisely determine the location of the minimum. In this way, accuracy of the estimated neural response may be improved with fewer evaluations.

In one or more examples, the artifact may be removed from the ECAP using various methods, including, but not limited to, a standard method, artifact model method, high-pass filter method, or a correlation method, where each method uses the processing circuitry to determine the ECAP characteristic value.

In using the standard method (SM) to determine an ECAP characteristic value, waveforms $V_i(t)$ may be low-pass filtered (Kaiser filter, 11 tap, 4.5 kHz) to further band-limit and reduce asynchronous noise. In one or more examples, ECAP amplitude may be subsequently estimated (e.g., calculated) as a difference (e.g., in amplitude, such as in μV) between the P2 and N1 features of the ECAP. In one or more examples, N1 may be defined as the minimum amplitude of the filtered waveform in the temporal window from 0.3 to 0.6 milliseconds (ms), while P2 may be defined as the maximum amplitude in the temporal window from 0.7 to 1.1 ms. These windows of time may be set given the anticipated latencies and morphological characteristics of the ECAP. The latencies may be a function of the spacing between the stimulating and recording electrodes, along with the expected conduction velocity of ECAPs in the spinal cord. In case of a large artifact that starts positive and decays over time, it is possible that the N1 is greater than P2, where the N1-P2 may be computed to be negative.

The processing circuitry 210 may also, or alternatively, use an artifact model (AM) to determine a ECAP characteristic value. In one or more examples, the stimulation artifact may be composed of two decaying exponentials with different time constants. In one or more examples, over a relatively short post-stimulation window for estimating spinal ECAPS, for example, 1.5 ms, an artifact may be suitably modeled as the sum of a single exponential plus a linear component, which may more accurately estimate the ECAP amplitude. If $V_i(t)$ is the recorded voltage waveform after averaging, the estimate of artifact A(t) may be obtained by optimally fitting the following equation to data $V_i(t)$:

$$A(t) = c_1\exp(-t/\tau) + c_2 t + c_3$$

The fit may be performed by determining the minimum in the following error function over parameters c1, c2, c3, and τ:

$$E(c_1, c_2, c_3, \tau) = \sum_t (V(t) - A(t))^2$$

To solve this optimization problem, t may be varied from 50 to 800 ρs in 100 logarithmic steps. For each τ, E(τ) may BE determined by solving the following closed-form matrix equation:

$$M = \begin{bmatrix} \exp\left(-\frac{t_0}{\tau}\right) & t_0 & 1 \\ \exp\left(-\frac{2t_0}{\tau}\right) & 2t_0 & 1 \\ \cdots & \cdots & \cdots \end{bmatrix}$$

$$C = (M'M)\backslash(M'V)$$

$$E(\tau) = \text{Norm}\,(V - MC)$$

In the above equation, $t_0$ may be the sampling period, C is a 3×1 vector of optimal e coefficients, V may be a vector composed of measured samples V(t), and Norm may represent a norm-2 operation. Optimal t may be determined to be one that produced the smallest E(τ). The equation above was utilized to compute the C coefficients. After the artifact model is determined, the N1−P2 amplitude may be calculated or estimated from the denoised waveform V(t)−A(t) using the same N1 and P2 windows as in the standard method.

In one or more examples, the processing circuitry 210 may also, or alternatively, use a high-pass filter (HP) method. For example, the stimulation artifact may contain lower-frequency content relative to the ECAP in the later portion of the biopotential recording (e.g., greater than 0.6 ms after the end of the stimulation pulse). As such, another approach for mitigating the stimulation artifact overlapping the ECAP may be application of a high pass or differentiator filter. Such a filter may have the following benefits. The first peak response of the differentiator occurs at the high-slope transition of the ECAP from N1 to P2. This response may be delayed relative to N1, the first feature of the ECAP used by the SM to estimate the ECAP, and advantageously results in extra temporal isolation between the signal and the artifact with the differentiator. In addition, a simple differentiator may be implemented in a very computationally efficient manner, an important consideration for battery powered implantable medical devices.

A comb filter with response $1-z^{-2}$ may be utilized as a differentiator for the acquired biopotentials. After application of the differentiator filter, the waveform may be smoothed (Kaiser, FIR 11 tap filter; cutoff 4.5 kHz). The ECAP response may be computed as the difference between the maximum output in the temporal window from approximately 0.6 to 0.85 ms to the minimum output in the window from approximately 0.9 to 1.125 ms. The temporal windows may be set using similar considerations to those employed with the standard method.

The processing circuitry 210 may also, or alternatively, use a correlation method (CM) which estimates spinal cord activation by correlating the acquired biopotential with a synthesized filter template, T(t). Specifically, the neural response may be computed as:

$$N_i = \sum_t T(t) * V_i(t - \Delta)$$

The template used here may have a mathematical expression of T(t)=B(t) sin(4πt/1.3)/N, where t is time in ms, B(t) is the Bartlett window, and N is the normalization factor, N=sum(B(t)2 sin(4πt/1.3)2) over a 1.3-ms window, for example. The template may approximate the morphology of a typical ECAP signal. A duration of 1.3 ms may be used to optimize the match of the template with the observed response. The template may be orthogonal to the first three components of a Taylor expansion of the artifact waveform, namely the constant term, the linear term and the quadratic term. Thus, when the template is applied to a waveform containing both neural response and artifact, the artifact component may be reduced. However, variable latencies in neural responses routinely occur due to the differences in conduction velocities across subjects and delay in action potential initiation across stimulation levels or pulse width. The template may be matched to the neural recording and Fourier techniques may be utilized accordingly to compute the optimal delay, Δ.

$$A_i = \sum_t \frac{B(t)\sin(4\pi t/1.3)}{N} * V_i(t)$$

$$A_r = \sum_t \frac{B(t)\cos(4\pi t/1.3)}{N} \times V_i(t)$$

$$\Delta(\text{ms}) = -\left(\frac{\angle(A_i - A_R 1j)}{4\pi}\right)1.3$$

In some examples, to account for variability in neural response latencies, while avoiding non-physiological shifts in the response, the system may prevent A from decreasing below 0 or increasing above 0.18 ms.

Figure 5A:
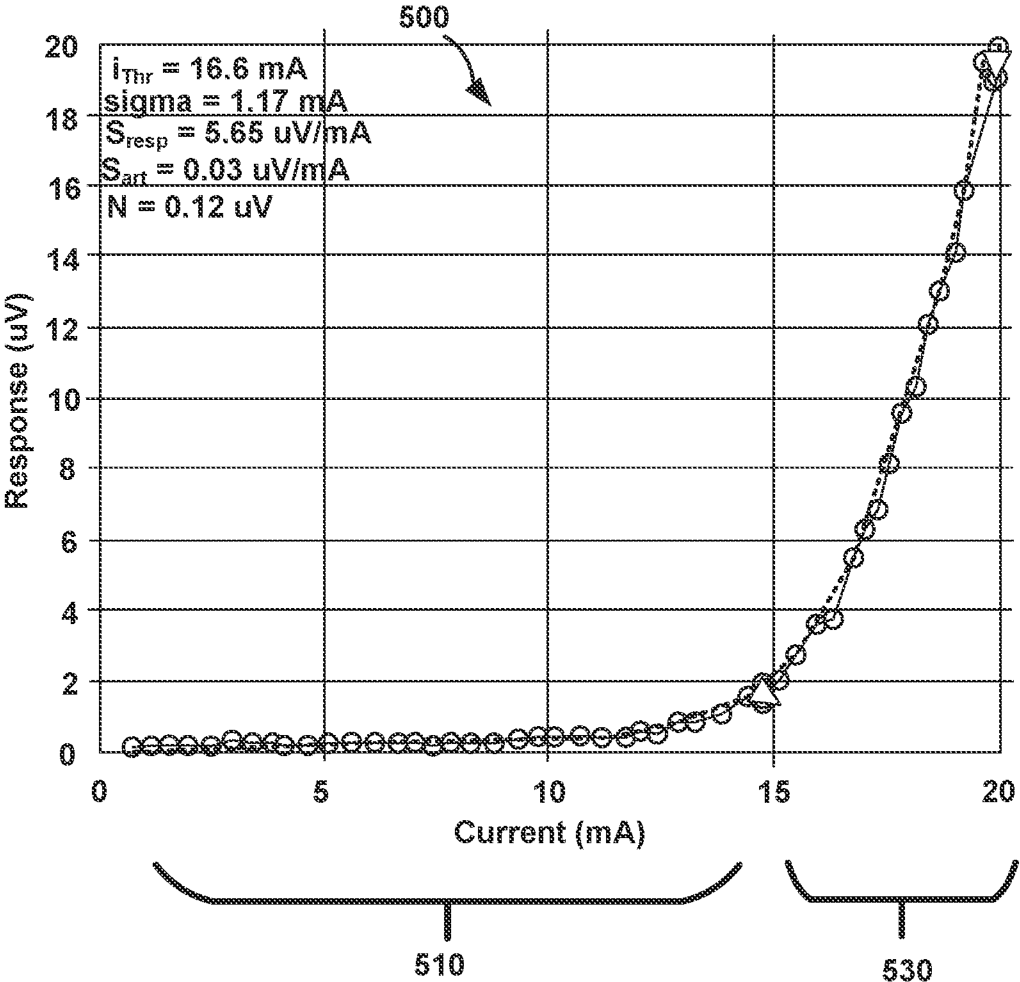
FIG. 5A is an example growth curve of characteristic values for sensed ECAPs.
Figure 5B:
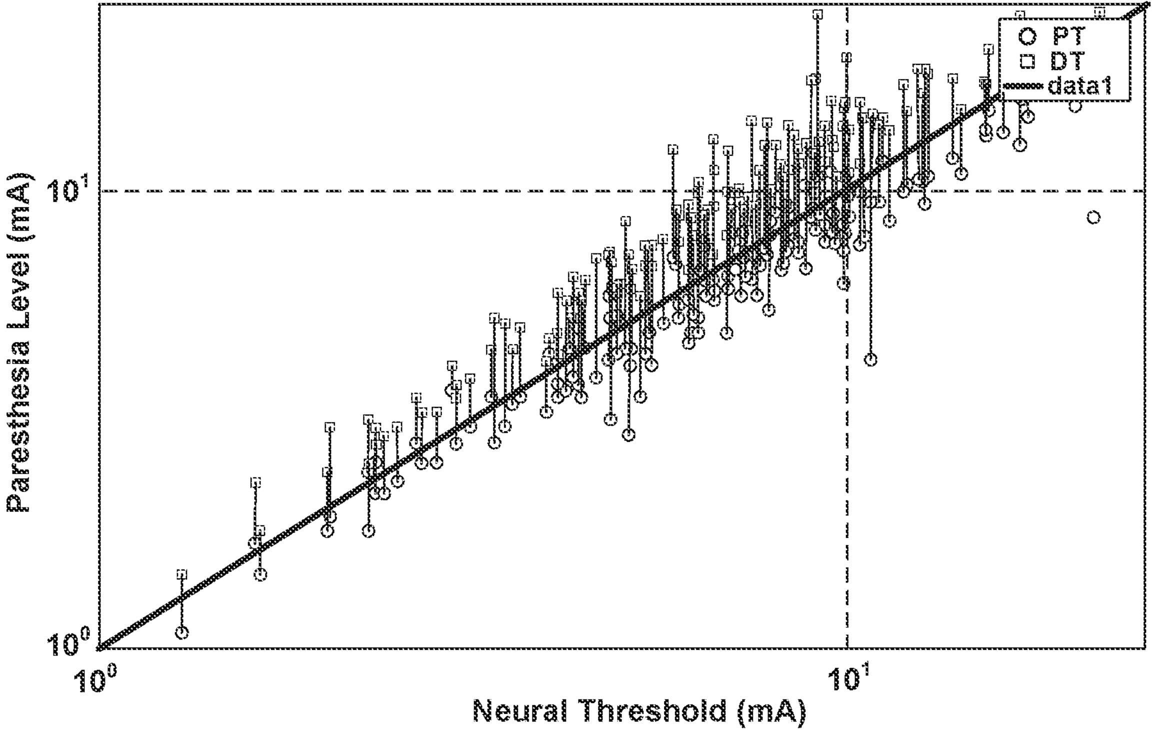
FIG. 5B is a graph of data of the perception threshold and estimated neural threshold.

Once the ECAP characteristic value has been determined, the value may be used to determine an estimated neural threshold. A patient threshold of stimulation (for example, a perception threshold that represents the minimal stimulation current that causes a patient to feel the stimulation) may be correlated to the neural threshold. For example, FIG. 5B shows a relationship between estimated neural threshold and determined paresthesia levels (e.g., perception and discomfort thresholds) for various subjects. The estimated neural threshold may be automatically calculated based on ECAP signals as described herein, and the determined perception thresholds and discomfort thresholds may be determined based on patient feedback to different stimulation amplitudes. Each pair of perception threshold and discomfort threshold for a patient is shown as a vertical line, with the perception threshold value below the lower value and the discomfort threshold being the higher value. As shown in FIG. 5B, the determined paresthesia levels for stimulation is tightly correlated to the estimated neural threshold. In other words, the estimated neural threshold was determined to fall between the perception threshold and the discomfort threshold for each subject. In one or more examples, a growth curve or a correlation curve may be developed that defines a relationship between ECAP characteristic values for different stimulation amplitudes (FIG. 5A). Processing circuitry 210 may generate the growth curve by controlling stimulation circuitry to deliver stimulation pulses while sweeping the stimulation amplitude (e.g., iteratively increasing the amplitude) to sense respective ECAP signals and obtain ECAP characteristic values (e.g., data), which represents an estimated neural response. In one or more embodiments, a storage device may store data which may define a correlation curve (e.g., a growth curve) defining a relationship between the ECAP characteristic values and stimulation amplitude. The system may determine the estimated neural thresholds based on this correlation curve. The estimated neural threshold may represent the estimated stimulation amplitude at which the patient response would transition from sub-perception, to perception of stimulation. The system may set an initial amplitude for stimulation based on the estimated neural threshold or set a target ECAP value for therapy using the estimated neural threshold (e.g., below, at, or above the neural threshold of the patient). In some examples, near the neural threshold of the patient, there may be a substantial curvilinear component, such as the beginning of an inflection portion of the correlation curve. In one or more examples, a non-physiologic component of the response can occasionally manifest below the neural threshold. In some examples, the response can grow linearly with increasing current and may be related to the residual artifact.

In one or more examples, as shown in FIG. 5A, the growth curve 500 from ECAP signals detected at the spinal cord may include a first region 510, which may be substantially linear. In some examples, the first region 510 of the growth curve 500 may be calculated where a change in amplitude is defined in part by a residual artifact to calculate the ECAP characteristic value. In some examples, the first region 510 may be the curve below 15 mA of current. In some examples, which may depend on the method used to determine the ECAP characteristic value, a non-physiologic component of the response may manifest occasionally below the estimated neural threshold. The response grows linearly with increasing current and may be related to the residual artifact. In a second region 530 of the growth curve 500, a change in amplitude is defined in part by patient neural response. In one or more examples, near the estimated neural threshold there may be a substantial curvilinear component. In some examples, determining the estimated neural threshold is determined at least in part on a curvature of an inflection region of the growth curve 500. In some examples, the second region 530 may be characterized by threshold ($I_{thr}$) and sigma (how fast response grows in this region). In one or more examples, a width of the curve relates to a therapeutic range of parameter settings offered to the patient and/or clinician.

In one or more examples, the following functional form may represent the first region 510 and the second region 530, for example, both the physiologic and artifact-driven, non-physiologic contributions to the ECAP growth curve 500:

$$E(I) = R(I, I_{thr}, \sigma) \cdot S_{Resp} + I \cdot S_{art} + N$$

$$R(I, I_{thr}, \sigma) = \left(\sigma \log\left(\exp\left(-\frac{I - I_{thr}}{\sigma}\right) + 1\right) + (I - I_{thr})\right)$$

In one or more examples, the estimate of neural activation, E(I), at a given stimulation current, I, may be the sum of three components. The components may include $R(I, I_{thr}, \sigma) \cdot S_{Resp}$, which captures the contribution of a neural response to the growth curve; $S_{art}$, which describes a rate of growth of the artifact with current; and constant N, which is utilized to fit residual noise. The neural contribution may be characterized by parameters $I_{thr}$, σ, and $S_{Resp}$. $I_{thr}$ represents the estimated threshold for neural activation, while σ represents the spread, a parameter that defines how quickly the curve transitions between the curvilinear and linear region as stimulation current is increased. $S_{resp}$ describes the rate of growth of neural response in the linear region. An example of the fit along with the parameters is shown FIG. 5A.

FIGS. 6A-D through 8A-D show three example responses recorded from a human subject that capture the types of the interaction between artifact for the ECAP signal and response encountered. FIGS. 6A, 7A, and 8A show the waveforms $V_i(t)$; FIGS. 6B, 7B, and 8B show outputs of the AM methods of determining ECAP characteristic values, FIGS. 6C, 7C, and 8C show outputs of the HP methods of determining ECAP characteristic values, and FIGS. 6D, 7D, and 8D show the resulting growth curves (symbols) together with their best fits (lines) for four exemplary techniques for calculating ECAP characteristic values, for example, by processing circuitry.

In the case shown in FIGS. 6A-D, the artifact is flat relative to the neural response, and the neural responses are clearly visible even in the standard method (FIG. 6A). In this case, the AM method (FIG. 6B) results in responses that are very similar to those seen in the raw traces. The HP method (FIG. 6C) shifts the dominant component of the response from N1 trough (in this case at approximately at 0.4 ms) to a positive peak at approximately 0.7 msec. Turning to the growth curves (FIGS. 6D, 7D, 8D), the standard method is represented by star-shaped data points, the AM method is represented by circular data points, the HP method by square-shaped data points, and the CM by diamond-shaped data points. As shown in the figures, the AM produces the growth curve that is closest to the one achieved with the standard method. The growth curves with the HP and CM approaches underestimate the neural response (second region 530 of FIG. 5A); however, the estimated threshold $I_{thr}$ for neural activation is similar across methods (Table 1).

In the cases shown in FIGS. 7A-D and 8A-D, the recorded traces $V_i(t)$ contain both substantial artifacts as well as characteristic neural responses (FIGS. 7A, 8A). The growth curve for the standard method shows substantial growth at levels below those where neural response is presumably occurring, in the case where the artifact starts out negative and decays towards zero. In contrast, the growth cure becomes negative and then reverses to positive where the artifact starts out positive and decays to zero (FIG. 8D). In all cases, the AM substantially attenuates the artifact and reveals the neural response, as shown in FIGS. 6B, 7B, and 8B. The HP filter exhibits a relatively large artifact early in the response, but the HP filter attenuates the artifact substantially later in the response (e.g., at t>0.6 ms).

In one or more examples, the qualitative observations discussed above may be captured quantitatively by examining the parameters of the fit for these examples; specifically, the degree of residual artifact may be captured by $S_{art}$, while the degree of preservation of the neural response may be captured by comparing to the neural growth slope parameter $S_{resp}$ (Table 1). The parameters of the fit of the growth curve may be utilized to quantify the effectiveness of these ECAP characteristic value development, for example to cancel artifacts while preserving the neural response.

Table 1 shows parameters of the fit for the three examples in FIGS. 6D, 7D, and 8D. Of Table 1, Columns 3 and 4 show the amount of artifact ($S_{art}$) and neural contribution ($S_{resp}$) to the ECAP characteristic value, respectively. Column 5 shows the calculated threshold of neural activation ($I_{thr}$).

TABLE 1

| Condition | Artifact Method | $S_{art}$ (μV/mA) | $S_{resp}$ (μV/mA) | $I_{thr}$ (mA) |
|---|---|---|---|---|
| FIG. 6 | Standard | −0.64 | 75.99 | 3.7 |
| | AM | 0.31 | 70.37 | 3.7 |
| | HP | −0.21 | 38.06 | 3.6 |
| | CM | 0.08 | 42.51 | 3.8 |
| FIG. 7 | Standard | 1.83 | 10.84 | 5.6 |
| | AM | 0.05 | 10.97 | 5.9 |

TABLE 1-continued

| Condition | Artifact Method | $S_{art}$ (μV/mA) | $S_{resp}$ (μV/mA) | $I_{thr}$ (mA) |
|---|---|---|---|---|
| | HP | 0.17 | 5.67 | 5.6 |
| | CM | −0.21 | 6.19 | 5.6 |
| FIG. 8 | Standard | −0.09 | 7.74 | 4.8 |
| | AM | 0.01 | 8.15 | 4.6 |
| | HP | −0.01 | 4.94 | 4.6 |
| | CM | 0.16 | 5.32 | 4.5 |

Figure 9:
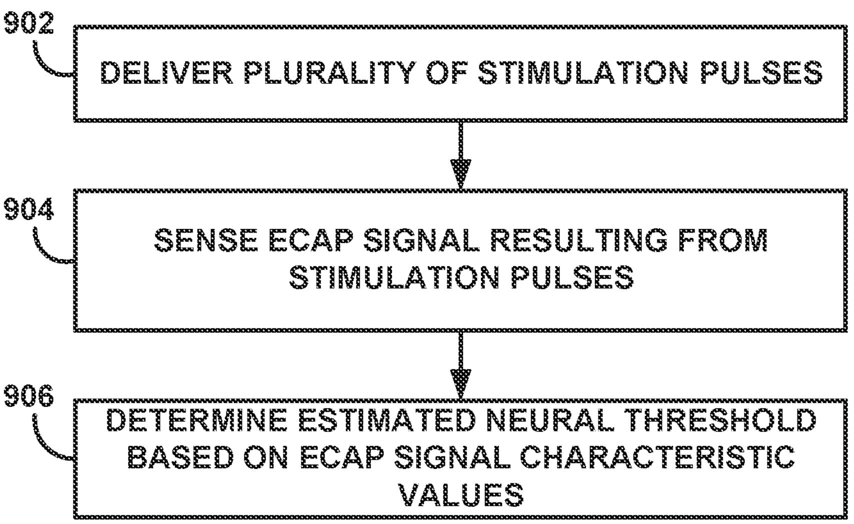
FIG. 9 is a flow diagram illustrating an example technique for determining an estimated neural threshold.

FIG. 9 is a flow diagram illustrating an example technique for determining an estimated neural threshold based on ECAP signal characteristic values. IMD 200 and processing circuitry 210 will be described in the example of FIG. 9, but other IMDs, such as IMD 110, or other devices (e.g., external programmer 150) or systems may perform, or partially perform, the technique of FIG. 9.

In one or more examples, processing circuitry 210 controls IMD 200 to deliver a plurality of stimulation pulses (902). In some examples, each stimulation pulse of the plurality of stimulation pulses is at least partially defined by a different respective value of a stimulation parameter. In this manner, the different values of the stimulation parameter may constitute a sweep of increasing stimulation amplitudes that may be linear, non-linear, adaptive based on feedback, and/or some combination thereof.

The processing circuitry 210 may also control IMD 200 to sense the respective ECAP signals resulting from the stimulation pulses (904). In some examples, the method may include receiving, by the processing circuitry, evoked compound action potential (ECAP) signal information, wherein the ECAP signal information comprises ECAP signals sensed by sensing circuitry and elicited by the plurality of stimulation pulses, and determining, by the processing circuitry and based on the ECAP signal information, ECAP characteristic values for each of the ECAP signals elicited by the plurality of stimulation pulses. In some examples, the ECAP characteristic value may comprise a direct measurement, by processing circuitry, between an N1 peak and a P2 peak of the ECAP signal information. In some examples, the ECAP characteristic values may comprise the ECAP signal information with an artifact removed therefrom. In one or more examples, removing the artifact may include modeling, for example by the processing circuitry, the artifact as a sum of a single exponential component plus a linear component, and removing the sum from each ECAP signal. In yet another example, the artifact may be sufficiently modeled solely as a linear component or exponential. In some examples, modeling the artifact by the processing circuitry includes estimating a minimum of an error function by weighting the error function higher in a first region than in a second region, where the first region is prior to a patient neural response and the second region is after the patient neural response. In one or more examples, removing the artifact includes passing the ECAP signal through a high-pass filter.

The method may further include determining, for example by processing circuitry 210 and based on the ECAP characteristic values, an estimated neural threshold of the patient (906). In some examples, the process of sensing the ECAP signals may include measuring the ECAP signals for a growth curve of a patient while the patient remains in the same position. In some examples, a correlation curve defines a relationship between ECAP characteristic values and stimulation amplitude, where the system can determine an estimated neural threshold based on the correlation curve (e.g., the growth curve). In some examples, the method may include storing data on a storage device 212, the data defining a correlation curve defining a relationship between ECAP characteristic values and stimulation amplitude, where the correlation curve includes a first region where change in amplitude is defined in part by residual artifact, and a second region where change in amplitude is defined in part by patient neural response, where the first region is prior to the estimated neural threshold and the second region is after the neural threshold. In some examples, determining the estimated neural threshold includes at least determining the estimated neural threshold at least in part on a curvature of an inflection region of the curve.

In some examples, the relationship of the sensed ECAP signal to the stimulation amplitude can be defined by:

$$E(I) = R(I, I_{thr}, \sigma)\cdot S_{Resp} + I\cdot S_{art} + N;$$

where:

$$R(I, I_{thr}, \sigma) = \left(\sigma\log\left(\exp\left(-\frac{I - I_{thr}}{\sigma}\right) + 1\right) + (I - I_{thr})\right);$$

- E(I) comprises the estimated neural response at a given stimulation current I;
- $I_{thr}$ comprises an ECAP threshold;
- σ comprises a parameter defining a rate of transition between a linear region of data and a curved region of data;
- $S_{art}$ comprises is a rate of growth of an artifact with current; and
- $S_{resp}$ comprises a rate of growth in the linear region of data.

Figure 10:
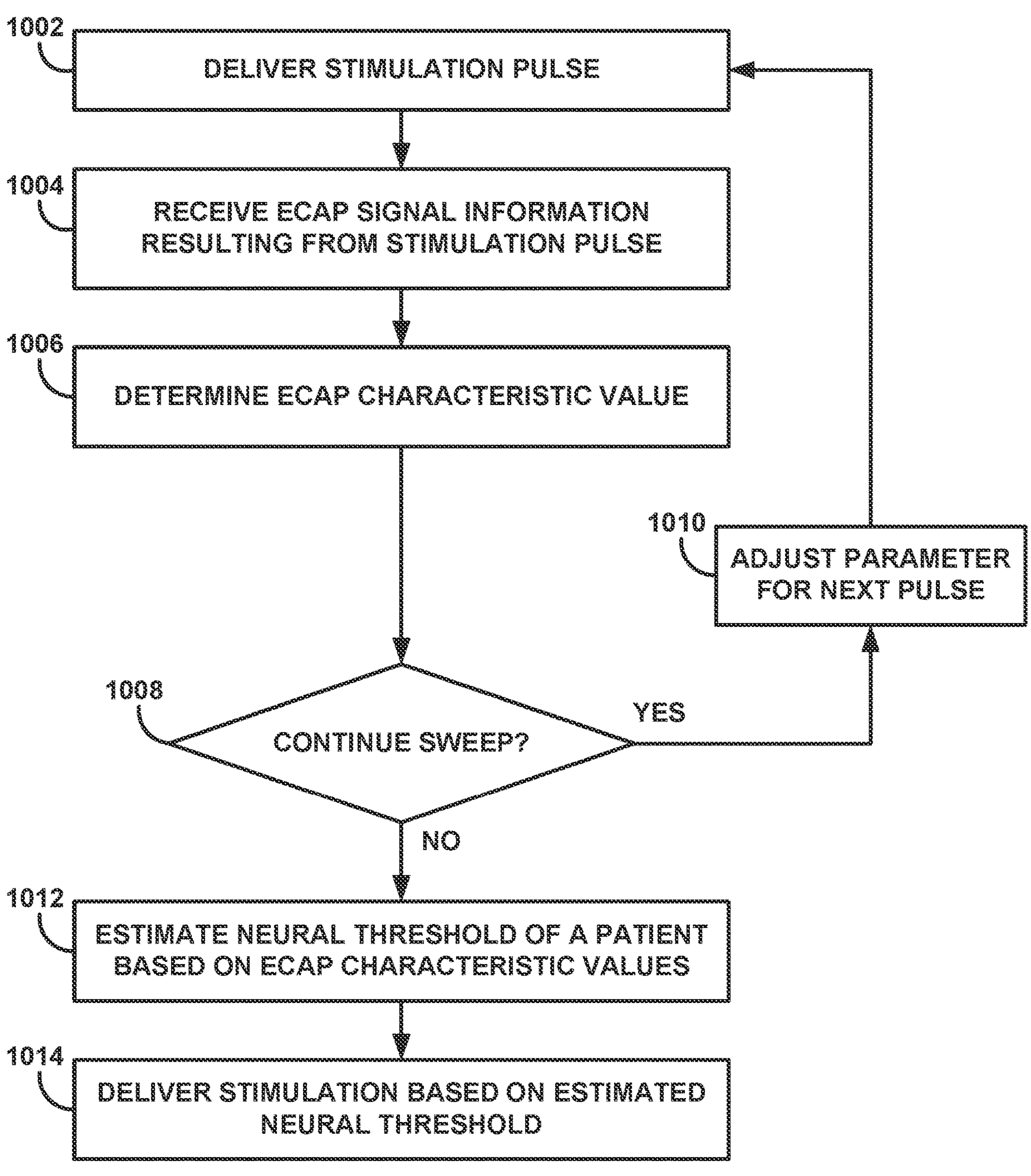
FIG. 10 is a flow diagram illustrating an example technique for determining an estimated neural threshold and delivering electrical stimulation.

FIG. 10 is a flow diagram illustrating an example technique for determining an estimated neural threshold based on ECAP signal characteristic values. IMD 200 and processing circuitry 210 will be described in the example of FIG. 10, but other IMDs, such as IMD 110, or other devices or systems may perform, or partially perform, the technique of FIG. 10.

In one or more examples, processing circuitry 210 controls IMD 200 to deliver a stimulation pulse (1002). The stimulation pulse is at least partially defined by a respective value of a stimulation parameter. The processing circuitry 210 may also control IMD 200 to sense ECAP signals resulting from the stimulation pulse. In some examples, processing circuitry 210 may receive, by the processing circuitry 210, evoked compound action potential (ECAP) signal information (1004). In one or more examples, the ECAP signal information may include ECAP signals sensed by sensing circuitry and elicited by the stimulation pulse.

In one or more examples, the method includes determining, for example by processing circuitry 210, ECAP characteristic value(s) for the ECAP signals elicited by the stimulation pulses, where the ECAP characteristic value(s) are based on the ECAP signal information (1006). In some examples, the ECAP characteristic value may comprise a direct measurement, by processing circuitry 210, between an N1 peak and a P2 peak of the ECAP signal information. In some examples, the ECAP characteristic values may comprise the ECAP signal information with an artifact removed therefrom.

In one or more examples, removing the artifact may include modeling, for example by processing circuitry 210, the artifact as a sum of a single exponential component plus a linear component, and removing the sum from each ECAP signal. In some examples, modeling the artifact by processing circuitry 210 includes estimating a minimum of an error function by weighting the error function higher in a first region than in a second region, where the first region is prior to a patient neural response and the second region is after the patient neural response. In one or more examples, removing the artifact comprises passing, for example by processing circuitry 210, the ECAP signal through a high-pass filter.

The processing circuitry 210 then determines whether to continue with a sweep of different parameter values (1008). The sweep may include iteratively increasing a stimulation parameter value, such as an amplitude, for successive stimulation pulses. The processing circuitry 210 may determine to continue to sweep if the parameter value is not yet at a predetermined value, if an estimated neural threshold cannot be determined from already collected ECAP characteristic values, or if processing circuitry 210 has not received patient input requesting to stop the sweep. The processing circuitry 210 may stop the sweep in response to the parameter value reaching the predetermined value, in response to determining that the neural threshold can be determined, or in response to receiving patient input requesting to stop the sweep (e.g., when stimulation amplitude has reached a discomfort threshold). If processing circuitry 210 determines to continue the sweep ("YES" branch of block 1008), processing circuitry 210 adjusts the parameter value (e.g., increases the stimulation amplitude) for the next pulse (1010) and continues to control IMD 200 to deliver the next stimulation pulse (1002).

If processing circuitry 210 determines to stop the sweep ("NO" branch of block 1008), processing circuitry 210 estimates the neural threshold of a patient based on ECAP characteristic values (1012). For example, the method may further include determining, for example, by processing circuitry 210 and based on the ECAP characteristic values, an estimated neural threshold of the patient.

In some examples, processing circuitry 210 senses ECAP signals for measuring a growth curve of a patient while the patient remains in the same position. In some examples, the IMD 200 or the system 100 may detect portions of time when no motion is occurring, for example, by use of an artifact or a sensor such as an accelerometer. In some examples, a correlation curve defines a relationship between ECAP characteristic values and stimulation amplitude, where the correlation curve is used for the growth curve to determine an estimated neural threshold. In some examples, the method may include storing data on a storage device 212, the data defining a correlation curve defining a relationship between ECAP characteristic values and stimulation amplitude, where the correlation curve includes a first region where change in amplitude is defined in part by residual artifact, and a second region where change in amplitude is defined in part by patient neural response, where the first region is prior to the estimated neural threshold and the second region is after the neural threshold. In some examples, determining the estimated neural threshold is determined at least in part on a curvature of an inflection region of the curve.

In some examples, the relationship is defined by:

$$E(I) = R(I, I_{thr}, \sigma)\cdot S_{Resp} + I\cdot S_{art} + N;$$

where:

$$R(I, I_{thr}, \sigma) = \left(\sigma\log\left(\exp\left(-\frac{I - I_{thr}}{\sigma}\right) + 1\right) + (I - I_{thr})\right);$$

E(I) comprises the estimated neural response at a given stimulation current I;

$I_{thr}$ comprises an ECAP threshold;

σ comprises a parameter defining a rate of transition between a linear region of data and a curved region of data;

$S_{art}$ comprises is a rate of growth of an artifact with current; and $S_{resp}$ comprises a rate of growth in the linear region of data.

Processing circuitry 210 may then deliver stimulation pulses based on the estimated neural threshold (1014). For example, processing circuitry 210 may set the initial amplitude values to the estimated neural threshold or determine a target ECAP value based on some percentage or multiplier of the estimated neural threshold. Once the neural threshold has been estimated, processing circuitry 210 may deliver and/or adjust stimulation pulses.

Based on the ECAP characteristic value and estimated neural threshold, processing circuitry 210 can determine a parameter value for subsequent electrical stimulation pulses. For example, if the ECAP characteristic value is above or below a target characteristic value, processing circuitry 210 may reduce or increase, respectively, the value of a parameter that defines subsequent stimulation pulses. In one or more examples, processing circuitry 210 uses a target ECAP characteristic value associated with a percentage above or below the estimated neural threshold. Processing circuitry 210 then controls stimulation circuitry to deliver electrical stimulation at least partially defined by the adjusted value of the parameter. For example, the parameter may be a current amplitude or pulse width of the stimulation pulses. Processing circuitry 210 may continue to perform the process of FIG. 10 in a loop to continually use characteristic values of ECAP signals as feedback for adjusting stimulation pulses.

Figure 11:
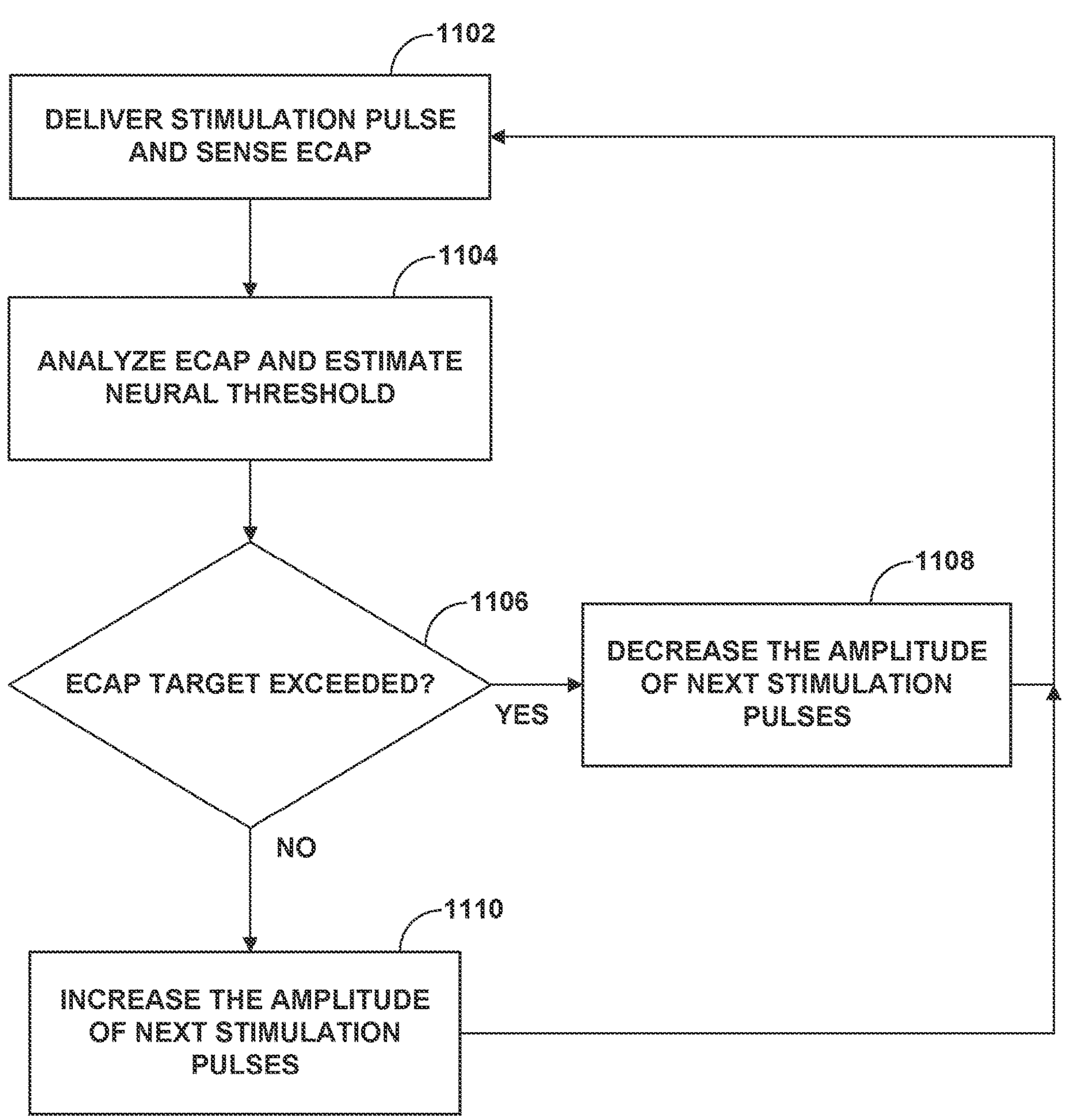
FIG. 11 is a flow diagram illustrating an example technique for determining estimated neural threshold and controlling electrical stimulation.

FIG. 11 is a flow diagram illustrating an example technique for adjusting stimulation therapy. For convenience, FIG. 11 is described with respect to IMD 200 of FIG. 2. However, the technique of FIG. 11 may be performed by different components of IMD 200 or by additional or alternative devices. The technique of FIG. 11 is an example feedback mechanism for controlling stimulation therapy using sensed ECAP signals.

As illustrated in FIG. 11, processing circuitry 210 of IMD 200 delivers a stimulation pulse and senses the resulting ECAP elicited by the stimulation pulse (1102). Processing circuitry 210 receives and analyzes the ECAP to determine an estimated neural threshold (as discussed above with respect to FIGS. 9 and 10) (1104). The estimated neural threshold, which is associated with patient sensory threshold or perception threshold, may be used to determine an ECAP target value. For example, the ECAP target value may be set to the estimated neural threshold or some percentage below or above the estimated neural threshold. The processing circuitry 210 evaluates whether the ECAP characteristic value has exceeded the target ECAP value (1106). In some examples, the processing circuitry 210 may target a lesser percentage than the ECAP characteristic value associated with the estimated neural threshold, for example to extend battery life of IMD 200. For example, processing circuitry 210 may target 70% of the estimated neural threshold. In some examples, a neural threshold target may include a range of values. In one or more examples, a neural threshold target may include a range of 30% of the estimated neural threshold to an upper limit of below a discomfort threshold for a patient.

If processing circuitry 210 determines that the representative amplitude of the one or more ECAP signals is greater than the target ECAP value ("YES" branch of block 1106), processing circuitry 210 decreases the amplitude of the next stimulation pulses (1108). For example, the amplitudes of the stimulation pulses may be decreased by predetermined steps. As another example, the respective amplitudes of the stimulation pulses may be decreased by an amount proportional to the difference between the representative amplitude and the ECAP characteristic value associated with the neural response. If processing circuitry 210 determines that the representative characteristic value is less than the ECAP characteristic value for the target neural response, ("NO" branch of block 1106), processing circuitry 210 moves to block 1110.

At block 1110, processing circuitry 210 increases the amplitude of the stimulation pulses by an amount proportional to the difference between the representative amplitude and the target ECAP characteristic value. Processing circuitry 210 then continues to deliver a stimulation pulse according to the increased or decreased amplitudes. In some examples, the decrease or increase applied to the stimulation pulses in steps 1108 or 1110, respectively, may apply to the amplitude or another parameter of the next-scheduled stimulation pulse. In this manner, even if a decrease is applied to the next stimulation pulse, the overall new amplitude of the next stimulation pulses may still be greater than the previous stimulation pulse if the scheduled amplitude of the next stimulation pulse minus the decrease is still greater than the amplitude of the previous stimulation pulse.

Although the process of FIG. 11 is described for adjusting the amplitude of the stimulation pulses (e.g., control pulses and/or stimulation pulses), other parameter values may be changed in other examples. For example, sensed ECAP signals may be used to increase or decrease the pulse width of the stimulation pulse to adjust the amount of charge delivered to the tissue to maintain consistent volume of neural activation. In other examples, electrode combinations may be adjusted in order to deliver different amounts of charge and modify the number of neurons being recruited by each stimulation pulse. In other examples, processing circuitry 210 may be configured to adjust the pulse rate or duty cycle of the stimulation pulses.

In some examples, therapy, such as for SCS stimulation, may be programmed. For example, setting parameter values for therapy may be based on a patient sensory threshold. In some examples, the programming and/or closed-loop control of SCS stimulation may be based on estimated neural threshold, including the techniques for estimating neural threshold described herein. In one or more examples, determination of the estimated neural threshold may be performed by the patient. For example, the patient may be asked to stay in a certain position, for example with the patient programmer 150 (FIG. 1), and then growth curves would be measured by processing circuitry using the techniques described herein, and an estimated neural threshold would be determined. In some examples, if stimulation therapy becomes uncomfortable, the patient may terminate the stimulation.

In some examples, a configuration for measurement would be selected to facilitate a larger response, which may be different than one used for ECAP therapy. The above-described steps can be repeated by the patient to optimize therapy in various positions in combination with the position-sensor technology.

Once the estimated neural threshold is determined for each component of the program, stimulation parameters of a SCS stimulation program may be determined based on the estimated neural threshold. For example, amplitude level for stimulation pulses of each program can be set as a percentage of the estimated neural threshold (e.g., 65%). Alternatively, both neural thresholds and sigma can be utilized to estimate the stimulation levels. For example, stimulation can be set to neural threshold plus 1/sigma to get a nearly constant response.

In some instances, one can record changes in threshold in the presence of other stimulation (e.g., high-rate stimulation) and compare to lower-rate stimulation to determine proper dosing of higher-rate stimulation. In some examples, real-time measurements of ECAP signals may be used to determine ECAP characteristic values for the ECAP signals, and estimated neural thresholds may be determined. The real-time determination of estimated neural threshold may be utilized to set stimulation levels. For example, occasional measurements near a sensation threshold can be utilized to measure threshold and establish a "dose" (e.g., intensity, duration, etc.) for other components of stimulation. Alternatively, when a position of the person is changed, one can adjust the stimulation automatically based on best neural threshold.

Figure 12:
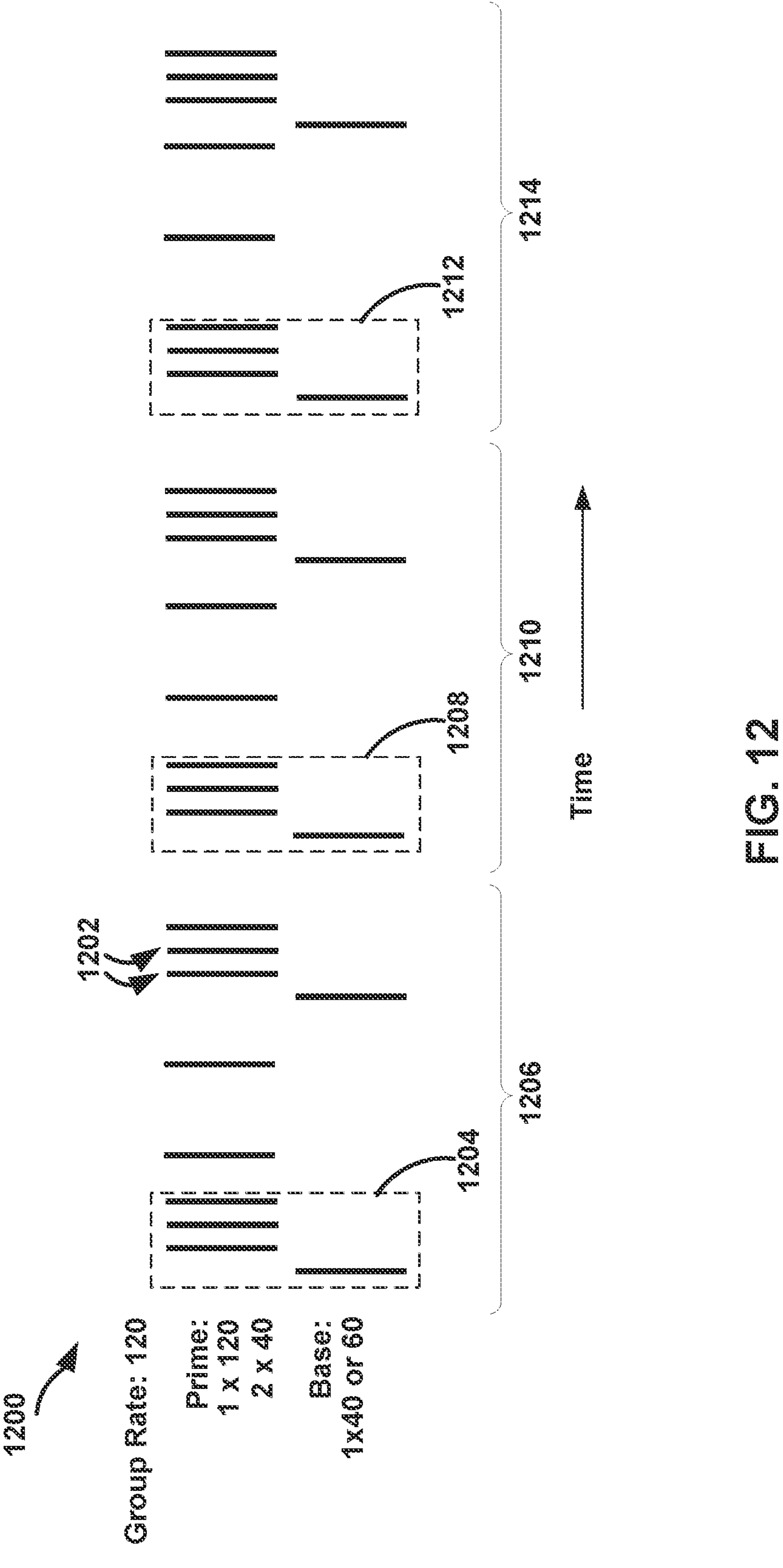
FIG. 12 is a timing diagram illustrating example electrical stimulation pulses delivered based on an estimated neural response.

FIG. 12 is a timing diagram illustrating an example of electrical stimulation pulses delivered according to different stimulation patterns. In one or more examples, the different amplitudes for stimulation pulses delivered via different electrode combinations (e.g., different tissue locations) may be determined based on an estimated neural threshold. As shown in timing diagram 1200, pattern cycles 1206, 1210, and 1214 are repeated groups of pulses over time. The top "prime" pulses can be delivered via one electrode combination and the bottom "base" pulses are delivered to a second electrode combination. Each of the pattern cycles are possible with a group rate of about 120 Hz (e.g., a system rate) for series of slots that includes 4 slots within which pulses 1202 can be delivered. In pattern 1206, series of slots 1204 has four slots where the first slot includes a pulse for the base stimulation to achieve 40-Hz stimulation, the second slot includes pulses for a 120-Hz pulse train, and the third and fourth slots include pulses for respective 40-Hz pulse trains for the prime stimulation. Therefore, the resulting prime stimulation is delivered with an average of 240 Hz and an interpulse frequency of 480 Hz for three consecutive pulses.

In pattern 1210, series of slots 1208 has four slots where the first slot includes a pulses for the base stimulation to achieve 40-Hz stimulation, the third slot includes pulses for a 120-Hz pulse train, and the second and fourth slots include pulses for respective 40-Hz pulse trains for the prime stimulation. Therefore, the resulting prime stimulation is delivered with an average of 240 Hz and an interpulse frequency of 480 Hz for three consecutive pulses.

In pattern 1214, series of slots 1212 has four slots where the first slot includes a pulses for the base stimulation to achieve 40-Hz stimulation, the fourth slot includes pulses for a 120-Hz pulse train, and the second and third slots include pulses for respective 40-Hz pulse trains for the prime stimulation. Therefore, the resulting prime stimulation is delivered with an average of 240 Hz and an interpulse frequency of 480 Hz for three consecutive pulses. Although a group rate of 120 is described, the group rate may be adjusted according to the number of slots in the series of slots and the desired frequencies to achieve for each type of stimulation. In other examples, the base stimulation may have a frequency of approximately 60 Hz. For any of the examples of herein, IMD 200 may switch the prime stimulation from one target tissue to another target tissue in order to achieve efficacious therapy.

In some examples, IMD 200 may change the order of pulses of one train of electrical stimulation pulses in the prime train with pulses of another train of electrical stimulation pulses over time to adjust a pulse pattern created by interleaving the at least of the electrical stimulation pulses of the trains of electrical stimulation pulses used to generate the overall prime train of stimulation pulses.

In some examples, the average frequency of the prime stimulation is selected from a frequency range from approximately 100 Hz to approximately 600 Hz. In another example, the average frequency of the prime stimulation is selected from a frequency range from approximately 150 Hz to approximately 300 Hz. In another example, the average frequency of the prime stimulation is approximately 200 Hz. The frequency of the base stimulation may be selected from a frequency range from approximately 40 Hz to approximately 60 Hz. In some examples, IMD 200 may include the amplitude of base stimulation until the patient achieves effective pain relief.

In some examples, IMD 200 may cycle between a first mode of a first period of time and a second mode of a second period of time, wherein the first mode comprises generating the first train of electrical stimulation pulses (e.g., the prime stimulation) at least partially interleaved with the second train of electrical stimulation pulses (e.g., the base stimulation). The second mode may include withholding generation of the first train of electrical stimulation pulses and the second train of electrical stimulation pulses. In some examples, the ratio of the first period to the second period of time is between approximately 1:1 and 1:3, inclusive. In other examples, the ratio may be lower to enable much longer "off" periods for stimulation. In one example, the first period of time for stimulation is selected from a range from approximately 1 minute to approximately 30 minutes. In another example, the first period of time for stimulation is selected from a range from approximately 5 minute to approximately 15 minutes. In some examples, the "on" period for stimulation may be less than 1 minute or greater than 30 minutes.

In some examples, the amplitude of pulses of the first train of electrical stimulation pulses (e.g., the prime stimulation) is below at least one of a perception threshold or a sensory threshold of a patient (e.g., below the estimated neural threshold). In some examples, the amplitude of pulses of the second train of electrical stimulation pulses (e.g., the base stimulation) is below at least one of a perception threshold or a sensory threshold of a patient (e.g., below the estimated neural threshold). In some examples, the prime stimulation is set at an amplitude value 60% of an estimated neural threshold of a patient. In some examples, the amplitude of pulses for the base stimulation is set at 65% of the estimated neural threshold of a patient. In this manner, the system may automatically determine the estimated neural threshold and, from the estimated neural threshold, the initial stimulation amplitude for the prime and base stimulation pulses.

The amplitude of a priming component may be set at a value below a Priming Perception Threshold (PPT), although setting it at or above the PPT is not excluded. The PPT may be found by slowly increasing the amplitude while feedback is obtained from the patient. Once the onset of perception is recorded, then the amplitude of the priming component may be changed to a value which is a percentage of the PPT (% PPT). Alternatively, the system may use the automatically determined estimated neural threshold instead of the PPT (or as the PPT). With an exemplary pulse frequency (PF) of about 200 Hz, the signal may be then set for a given time, e.g., about 10-30 minutes, before an electric component set at a tonic frequency lower than the PF, e.g., about 10 Hz to about 199 kHz, is applied independently to other electrodes in the lead. In the prime mode of stimulation, the tonic frequency will be lower than the priming frequency, but is not necessarily limited to a particular range of frequencies below the priming frequency.

In some examples, stimulation generation circuitry 202 may generate a first train of electrical stimulation pulses at a first frequency to a first target tissue, and may generate a second train of electrical stimulation pulses at a second frequency to a second target tissue different from the first target tissue. In some examples, at least some electrical stimulation pulses of the first train of electrical stimulation pulses may be interleaved with at least some electrical stimulation pulses of the second train of electrical stimulation pulses, and/or the first frequency may be greater than the second frequency. In one or more examples, processing circuitry 210 may determine amplitude values for the first and second trains of electrical stimulation pulses as respective percentages of the estimated neural threshold. These first and second trains may correspond to the prime stimulation and base stimulation, respectively.

Figure 13:
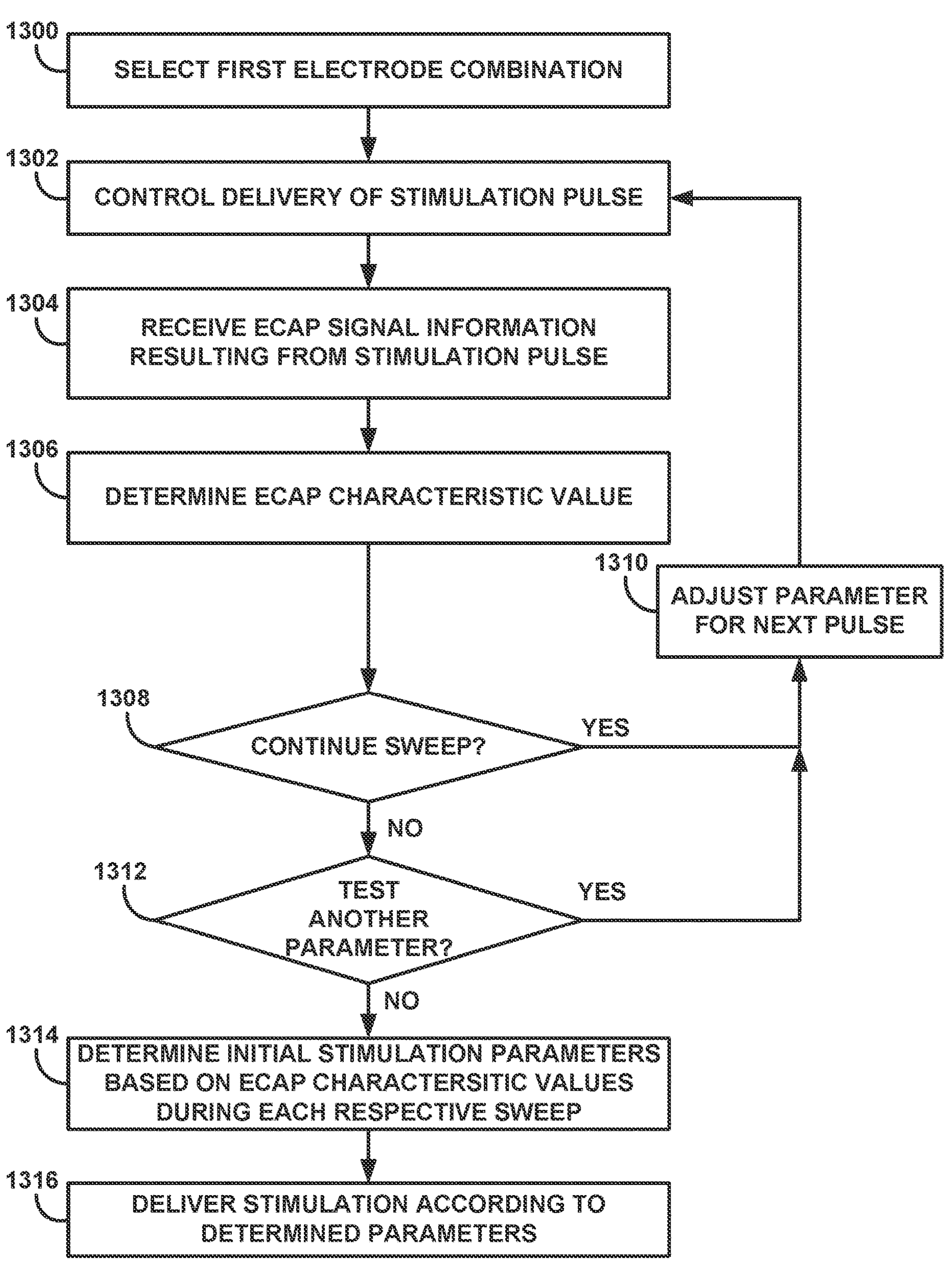
FIG. 13 is a flow diagram illustrating an example technique for automatically determining one or more parameter values for stimulation based on an ECAP characteristic.

FIG. 13 is a flow diagram illustrating an example technique for automatically determining one or more parameter values for stimulation based on an ECAP characteristic. As generally described herein, ECAP characteristics can be monitored from delivered stimulation because the ECAP characteristics can be indicative of how nerves respond (e.g., how many nerve fibers are depolarized to propagate the signal) to the delivered stimulation. One example of this phenomenon is the estimation of a neural threshold based on the growth curve of ECAP characteristic values such that the estimated neural threshold can be used to identify the stimulation amplitude that corresponds to the perception threshold of the patient. However, these techniques may also be used for a variety of stimulation parameters, such as amplitude, frequency, pulse width, stimulation electrode configuration, sensing electrode configuration, or any other parameters. Therefore, the system can sweep through different parameter values for respective stimulation pulses and automatically determine initial parameter values for electrical stimulation for the patient. This automatic parameter value determination may reduce the time needed for clinicians to spend manually determining parameters in the clinic and can enable re-calibration of parameter values over time if stimulation therapy becomes less effective, the patient's disease progresses, and the like.

As shown in the example of FIG. 13, a device and/or system can automatically determine stimulation parameter values based on ECAP characteristics. IMD 200 and processing circuitry 210 will be described in the example of FIG. 13, but other IMDs, such as IMD 110, or other devices or systems may perform, or partially perform, the technique of FIG. 13.

In one or more examples, processing circuitry 210 selects a first electrode combination to test (1300). The first electrode combination may be selected based on the implanted electrodes that are available (e.g., the electrodes located at one end of a lead), based on the location of electrodes with respect to target anatomy, or based on initial electrodes identified by a clinician, as some examples. Processing circuitry 210 then controls IMD 200 to deliver a stimulation pulse (1302). The stimulation pulse is at least partially defined by a respective value of a stimulation parameter. For example, a default pulse width and frequency may be used together with an initial low amplitude value with may be zero or close to zero. The processing circuitry 210 also controls IMD 200 to sense ECAP signals resulting from the stimulation pulse. In some examples, processing circuitry 210 may receive, by the processing circuitry 210, evoked compound action potential (ECAP) signal information (1304). In one or more examples, the ECAP signal information may include ECAP signals sensed by sensing circuitry and elicited by the stimulation pulse.

In one or more examples, the method includes determining, for example by processing circuitry 210, ECAP characteristic value(s) for the ECAP signals elicited by the stimulation pulses, where the ECAP characteristic value(s) are based on the ECAP signal information (1306). In some examples, the ECAP characteristic value may comprise a direct measurement, by processing circuitry 210, between an N1 peak and a P2 peak of the ECAP signal information. In some examples, the ECAP characteristic values may comprise the ECAP signal information with an artifact removed therefrom. As described herein, other examples may include calculating the amplitudes between different peaks, areas under peaks, the number of detectable peaks in the signal, etc.

In one or more examples, removing the artifact may include modeling, for example by processing circuitry 210, the artifact as a sum of a single exponential component plus a linear component, and removing the sum from each ECAP signal. In some examples, modeling the artifact by processing circuitry 210 includes estimating a minimum of an error function by weighting the error function higher in a first region than in a second region, where the first region is prior to a patient neural response and the second region is after the patient neural response. In one or more examples, removing the artifact comprises passing, for example by processing circuitry 210, the ECAP signal through a high-pass filter.

The processing circuitry 210 then determines whether to continue with a sweep of different parameter values (1308). The sweep may include iteratively increasing a stimulation parameter value, such as an amplitude, pulse width, or frequency, for successive stimulation pulses. The processing circuitry 210 may determine to continue to sweep if the parameter value is not yet at a predetermined value, e.g., if there is not enough ECAP characteristic data points to identify what parameter values are appropriate for stimulation. For example, processing circuitry 210 may continually attempt to identify changes in the ECAP characteristic, linear changes, inflection points, no further changes in ECAP characteristic values, etc. As soon as processing circuitry 210 can determine which value to use, processing circuitry 210 may determine to terminate the sweep. In some examples, processing circuitry 210 may repeat the sweep two or more times and/or sweep the parameter value back down using incrementally decreasing values. Processing circuitry 210 may thus obtain multiple ECAP characteristic values for the same parameter value over the multiple sweeps to develop more robust initial parameter values from this data. For example, processing circuitry 210 may average the ECAP characteristic values for each parameter value or determine a parameter value from each sweep and then average those determine parameter values to generate the initial parameter value for stimulation. In some examples, processing circuitry 210 may stop any sweep in response to determining that the patient has reached a discomfort threshold. If processing circuitry 210 determines to continue the sweep ("YES" branch of block 1308), processing circuitry 210 adjusts the parameter value (e.g., increases the stimulation amplitude) for the next pulse (1310) and continues to control IMD 200 to deliver the next stimulation pulse (1302).

If processing circuitry 210 determines to stop the sweep ("NO" branch of block 1308), processing circuitry 210 determines if another parameter or parameter value should be tested (1312). For example, processing circuitry 210 may determine that one or more different electrode combinations for delivering stimulation should be tested and run through the same sweeps to determine if more appropriate electrode combinations are available (e.g., stronger ECAP response to lower amplitude or lower pulse width, larger range of detectable ECAP signals, etc.). Processing circuitry 210 may also, or alternatively, test different sensing electrode combinations and similarly re-perform one or more sweeps of pulses to identify improved sensing electrode combinations Sweeps of other parameters may also be performed, such as for pulse width, frequency, pulse shape, active or passive recharge pulses, or any other desired parameters to review. Processing circuitry 210 may automatically determine which parameters to sweep based on pre-stored instructions, dynamically based on observed ECAP characteristics, or in response to clinician and/or patient input. If processing circuitry 210 determines to test another parameter ("YES" branch of block 1312), processing circuitry 210 selects or adjusts the parameter value for the next pulse (1310) and controls IMD 200 to deliver the next stimulation pulse (1302).

If processing circuitry 210 determines that no more parameters need to be tested ("NO" branch of block 1312), processing circuitry 210 determines the initial stimulation parameter values to be use based on the ECAP characteristic values obtained during each respective sweep (1314). For example, processing circuitry 210 may determine which stimulation electrode combination to use, which sensing electrode combination to use for sensing ECAP signals, the amplitude value to start using, and/or any other parameter values for pulse width, frequency, etc. In some examples, processing circuitry 210 may determine each parameter value that corresponds to an estimated neural threshold for that parameter or otherwise is based on the estimated neural threshold. However, processing circuitry 210 may alternatively use a calculation other than the estimated neural threshold for any or all of the determined parameter values.

In some examples, processing circuitry 210 senses ECAP signals for measuring a growth curve of a patient while the patient remains in the same position. In some examples, the IMD 200 or the system 100 may detect portions of time when no motion is occurring, for example, by use of an artifact or a sensor such as an accelerometer. Since patient movement may change the distance between nerves and the electrodes (stimulation or sensing electrodes), patient movement can corrupt the ECAP characteristics with respect to different parameter values during different patient positions. In some examples, processing circuitry 210 will pause a sweep until the movement stops, restart the sweep, or abort the process altogether and start again once the system determines that the patient's movement is stable or under some movement threshold (or even wait until the patient's posture is appropriate for sensing) In some examples, processing circuitry 210 may exclude ECAP characteristics that are determined to exceed some change threshold from a previously measured ECAP characteristic. For example, a 0.1 mA increase in amplitude should not cause an ECAP characteristic value that changes more than 10% from the previous amplitude. Processing circuitry 210 may exclude such threshold exceeding ECAP characteristic values, reperform stimulation for that parameter value, or abort the sweep and start again because the anomaly might affect subsequent measurements as well.

In some examples, a correlation curve defines a relationship between ECAP characteristic values and stimulation amplitude, where the correlation curve is used for the growth curve to determine the appropriate parameter value for stimulation. The initial parameter value may be determined to be lower than the estimated neural threshold parameter value (e.g., a certain percentage, such as a percentage between 10% and 90%), or at or above the estimated neural threshold parameter value. In some examples, the method may include storing data on a storage device 212, the data defining a correlation curve defining a relationship between ECAP characteristic values and stimulation parameter value, where the correlation curve includes a first region where change in amplitude is defined in part by residual artifact, and a second region where change in amplitude is defined in part by patient neural response. In some examples, determining the initial parameter value is determined at least in part on a curvature of an inflection region of the curve.

Processing circuitry 210 may then deliver stimulation pulses based on the determine parameter values (1316). For example, processing circuitry 210 may set the initial amplitude values and electrode combination to generate stimulation that will elicit the desired neural response which correlates to the calculated ECAP characteristic values. Processing circuitry 210 may repeat this technique periodically during therapy, in response to detecting that therapy is ineffective, or in response to patient or clinician input requesting that one or more parameter values are re-calculated. Although one example sequence for testing each parameter is described above, processing circuitry may test any parameter in any order in other examples.

The following numbered examples illustrate some techniques of this disclosure.

Example 1: In some examples, a method includes: controlling, by processing circuitry, delivery of a plurality of stimulation pulses to a patient, wherein each stimulation pulse of the plurality of stimulation pulses is at least partially defined by a different respective value of a stimulation parameter; receiving, by the processing circuitry, evoked compound action potential (ECAP) signal information, wherein the ECAP signal information comprises ECAP signals sensed by sensing circuitry and elicited by the plurality of stimulation pulses; determining, by the processing circuitry and based on the ECAP signal information, ECAP characteristic values for each of the ECAP signals elicited by the plurality of stimulation pulses; and determining, by the processing circuitry and based on the ECAP characteristic values, an estimated neural threshold of the patient.

Example 2: In some examples of the method of example 1, the method further includes controlling stimulation circuitry to generate and deliver stimulation therapy based on the estimated neural threshold.

Example 3: In some examples of the method of example 1 or example 2, the method further includes increasing, by the processing circuitry, a value of the plurality of stimulation parameters until the estimated neural threshold is determined.

Example 4: In some examples of the method of example 3, the stimulation parameter includes amplitude, pulse width, pulse rate, or duty cycle.

Example 5: In some examples of the method of any of examples 1-4, the method further includes storing data on a storage device, the data defining a correlation curve defining a relationship between ECAP characteristic values and stimulation amplitude, where the correlation curve includes a first region where change in amplitude is defined in part by residual artifact, and a second region where change in amplitude is defined in part by patient neural response, where the first region is prior to the estimated neural threshold and the second region is after the neural threshold.

Example 6: In some examples of the method of example 5, the estimated neural threshold is determined at least in part on a curvature of an inflection region of the curve.

Example 7: In some examples of the method of any of examples 1-6, the relationship is defined by:

$$E(I) = R(I, I_{thr}, \sigma) \cdot S_{Resp} + I \cdot S_{art} + N;$$

wherein:

$$R(I, I_{thr}, \sigma) = \left(\sigma \log\left(\exp\left(-\frac{I - I_{thr}}{\sigma}\right) + 1\right) + (I - I_{thr})\right);$$

- E(I) comprises the estimated neural response at a given stimulation current I;
- $I_{thr}$ comprises an ECAP threshold;
- σ comprises a parameter defining a rate of transition between a linear region of data and a curved region of data;
- $S_{art}$ comprises is a rate of growth of an artifact with current; and
- $S_{resp}$ comprises a rate of growth in the linear region of data.

Example 8: In some examples of the method of any of examples 1-7, the ECAP characteristic value comprises a direct measurement, by the processing circuitry, between an N1 peak and a P2 peak of the ECAP signal information.

Example 9: In some examples of the method of any of examples 1-4, the ECAP characteristic values include the ECAP signal information with an artifact removed therefrom.

Example 10: In some examples of the method of example 9, removing the artifact includes: modeling, by the processing circuitry, the artifact as a sum of a single exponential component plus a linear component; and removing the sum from each ECAP signal.

Example 11: In some examples of the method of example 10, modeling the artifact includes estimating a minimum of an error function by weighting the error function higher in a first region than in a second region, wherein the first region is prior to a patient neural response and the second region is after the patient neural response.

Example 12: In some examples of the method of example 9, removing the artifact includes passing, by the processing circuitry, the ECAP signal through a high-pass filter.

Example 13: In some examples of the method example 1, the method further includes: generating, by stimulation generation circuitry, a first train of electrical stimulation pulses at a first frequency to a first target tissue; generating, by the stimulation generation circuitry, a second train of electrical stimulation pulses at a second frequency to a second target tissue different from the first target tissue, wherein at least some electrical stimulation pulses of the first train of electrical stimulation pulses are interleaved with at least some electrical stimulation pulses of the second train of electrical stimulation pulses, and wherein the first frequency is greater than the second frequency; and determining, by the processing circuitry, amplitude values for the first and second trains of electrical stimulation pulses as respective percentages of the estimated neural threshold.

Example 14: In some examples, a system includes a memory, and processing circuitry configured to: control delivery of a plurality of stimulation pulses to a patient, wherein each stimulation pulse of the plurality of stimulation pulses are at least partially defined by a different respective value of a stimulation parameter; receive evoked compound action potential (ECAP) signal information, wherein the ECAP signal information comprises ECAP signals sensed by sensing circuitry and elicited by the plurality of stimulation pulses; determine, based on the ECAP signal information, ECAP characteristic values for each of the ECAP signals elicited by the plurality of stimulation pulses, and determine, based on the ECAP characteristic values, an estimated neural threshold of the patient.

Example 15: In some examples of the system of example 14, the processing circuitry is further configured to control stimulation circuitry to generate and deliver stimulation therapy based on the estimated neural threshold.

Example 16: In some examples of the system of example 14 or example 15, the processing circuitry is further configured to increase a value of the plurality of stimulation parameters until the estimated neural threshold is determined.

Example 17: In some examples of the system of example 16, the stimulation parameter includes amplitude, pulse width, pulse rate, or duty cycle.

Example 18: In some examples of the system of any of examples 14-17, the processing circuitry is further configured to store data on a storage device, the data defining a correlation curve defining a relationship between ECAP characteristic values and stimulation amplitude, wherein the correlation curve includes a first region where change in amplitude is defined in part by residual artifact, and a second region where change in amplitude is defined in part by patient neural response, and wherein the first region is prior to the estimated neural threshold and the second region is after the neural threshold.

Example 19: In some examples of the system of example 18, the estimated neural threshold is determined at least in part on a curvature of an inflection region of the curve.

Example 20: In some examples of the system of any of examples 14-19, the relationship is defined by:

$$E(I) = R(I, I_{thr}, \sigma) \cdot S_{Resp} + I \cdot S_{art} + N;$$

wherein:

$$R(I, I_{thr}, \sigma) = \left(\sigma \log\left(\exp\left(-\frac{I - I_{thr}}{\sigma}\right) + 1\right) + (I - I_{thr})\right);$$

- E(I) comprises the estimated neural response at a given stimulation current I;

$I_{thr}$ comprises an ECAP threshold;

σ comprises a parameter defining a rate of transition between a linear region of data and a curved region of data;

$S_{art}$ comprises is a rate of growth of an artifact with current; and $S_{resp}$ comprises a rate of growth in the linear region of data.

Example 21: In some examples of the system of any of examples 14-20, the ECAP characteristic value comprises a direct measurement, by processing circuitry, between an N1 peak and a P2 peak of the ECAP signal information.

Example 22: In some examples of the system of any of examples 14-21, the ECAP characteristic values comprise the ECAP signal information with an artifact removed therefrom.

Example 23: In some examples of the system of example 22, removing the artifact includes: modeling, by the processing circuitry, the artifact as a sum of a single exponential component plus a linear component; and removing the sum from each ECAP signal.

Example 24: In some examples of the system of example 23, to model the artifact, the processing circuitry is configured to: estimate a minimum of an error function by weighting the error function higher in a first region than in a second region, wherein the first region is prior to a patient neural response and the second region is after the patient neural response.

Example 25: In some examples of the system of example 22, to remove the artifact, the processing circuitry is configured to pass the ECAP signal through a high-pass filter.

Example 26: In some examples of the system claim 14, the system further includes stimulation generation circuitry configured to generate a first train of electrical stimulation pulses at a first frequency to a first target tissue; and generate a second train of electrical stimulation pulses at a second frequency to a second target tissue different from the first target tissue, wherein at least some electrical stimulation pulses of the first train of electrical stimulation pulses are interleaved with at least some electrical stimulation pulses of the second train of electrical stimulation pulses, and wherein the first frequency is greater than the second frequency; and wherein the processing circuitry is further configured to determine amplitude values for the first and second trains of electrical stimulation pulses as respective percentages of the estimated neural threshold.

Example 27: In some examples of the system of example 14, an implantable medical device comprises at least a portion of the processing circuitry.

Example 28: In some examples of the system of example 14, an external programming device comprises at least a portion of the processing circuitry.

Example 29: In some examples, a computer-readable storage medium includes instructions that, when executed by processing circuitry, cause the processing circuitry to: control delivery of a plurality of stimulation pulses to a patient, wherein each stimulation pulse of the plurality of stimulation pulses are at least partially defined by a different respective value of a stimulation parameter; receive evoked compound action potential (ECAP) signal information, wherein the ECAP signal information comprises ECAP signals sensed by sensing circuitry and elicited by the plurality of stimulation pulses, determine, based on the ECAP signal information, ECAP characteristic values for each of the ECAP signals elicited by the plurality of stimulation pulses; and determine, based on the ECAP characteristic values, an estimated neural threshold of the patient.

The techniques described in this disclosure may be implemented, at least in part, in hardware, software, firmware or any combination thereof. For example, various aspects of the described techniques may be implemented within one or more processors or processing circuitry, including one or more microprocessors, digital signal processors (DSPs), application specific integrated circuits (ASICs), field programmable gate arrays (FPGAs), or any other equivalent integrated or discrete logic circuitry, as well as any combinations of such components. The term "processor" or "processing circuitry" may generally refer to any of the foregoing logic circuitry, alone or in combination with other logic circuitry, or any other equivalent circuitry. A control unit including hardware may also perform one or more of the techniques of this disclosure.

Such hardware, software, and firmware may be implemented within the same device or within separate devices to support the various operations and functions described in this disclosure. For example, processing circuitry may conduct processing off-line and conduct automatic checks of patient ECAP signals and update programming from a remote location. In addition, any of the described units, circuits or components may be implemented together or separately as discrete but interoperable logic devices. Depiction of different features as circuits or units is intended to highlight different functional aspects and does not necessarily imply that such circuits or units must be realized by separate hardware or software components. Rather, functionality associated with one or more circuits or units may be performed by separate hardware or software components or integrated within common or separate hardware or software components.

The techniques described in this disclosure may also be embodied or encoded in a computer-readable medium, such as a computer-readable storage medium, containing instructions that may be described as non-transitory media. Instructions embedded or encoded in a computer-readable storage medium may cause a programmable processor, or other processor, to perform the method, e.g., when the instructions are executed. Computer readable storage media may include random access memory (RAM), read only memory (ROM), programmable read only memory (PROM), erasable programmable read only memory (EPROM), electronically erasable programmable read only memory (EEPROM), flash memory, a hard disk, a CD-ROM, a floppy disk, a cassette, magnetic media, optical media, or other computer readable media.

What is claimed is:

1. A system comprising:

processing circuitry configured to:

control delivery of a plurality of stimulation pulses to a patient, wherein each stimulation pulse of the plurality of stimulation pulses is at least partially defined by a different respective value of a stimulation parameter;

receive evoked compound action potential (ECAP) signal information, wherein the ECAP signal information comprises ECAP signals sensed by sensing circuitry and elicited by the plurality of stimulation pulses;

determine, based on the ECAP signal information, ECAP characteristic values for each of the ECAP signals elicited by the plurality of stimulation pulses;

determine a relationship between the ECAP characteristic values and the different respective values of the stimulation parameter; and determine, based on the relationship between the ECAP characteristic values and the different respective values of the stimulation parameter, an estimated neural threshold of the patient for stimulation.

2. The system of claim 1, wherein the processing circuitry is further configured to control stimulation circuitry to generate and deliver stimulation therapy based on the estimated neural threshold.

3. The system of claim 1, wherein the processing circuitry is further configured to iteratively increase the value of the stimulation parameter until the estimated neural threshold is determined.

4. The system of claim 3, wherein the stimulation parameter comprises one of a pulse amplitude, pulse width, pulse rate, or duty cycle.

5. The system of claim 1, wherein the stimulation parameter is a stimulation amplitude, wherein the processing circuitry is further configured to store data on a storage device, the data defining a correlation curve defining the relationship between the ECAP characteristic values and the different respective values of the stimulation amplitude, wherein the correlation curve includes a first region where change in the value of the stimulation amplitude is defined in part by residual artifact, and a second region where change in the stimulation amplitude is defined in part by patient neural response, and wherein the first region is prior to the estimated neural threshold and the second region is after the estimated neural threshold.

6. The system of claim 5, wherein the processing circuitry is configured to determine the estimated neural threshold at least in part on a curvature of an inflection region of the correlation curve.

7. The system of claim 6, wherein the relationship is defined by:

$$E(I) = R(I, I_{thr}, \sigma)\cdot S_{Resp} + I\cdot S_{art} + N;$$

wherein:

$$R(I, I_{thr}, \sigma) = \left(\sigma\log\left(\exp\left(-\frac{I - I_{thr}}{\sigma}\right) + 1\right) + (I - I_{thr})\right);$$

E(I) comprises an estimated neural response at a given stimulation current I;

$I_{thr}$ comprises an estimated threshold for neural activation;

σ comprises a parameter defining a rate of transition between a linear region of data and a curved region of data;

$S_{art}$ comprises is a rate of growth of an artifact with current; and $S_{resp}$ comprises a rate of growth in the linear region of data.

8. The system of claim 1, wherein one of the ECAP characteristic values comprises a direct measurement between an N1 peak and a P2 peak of the ECAP signal information.

9. The system of claim 1, wherein the ECAP characteristic values comprise the ECAP signal information with an artifact removed therefrom.

10. The system of claim 9, wherein, to remove the artifact, the processing circuitry is configured to:

model the artifact as a sum of a single exponential component plus a linear component; and remove the sum from each ECAP signal.

11. The system of claim 10, wherein, to model the artifact, the processing circuitry is configured to estimate a minimum of an error function by weighting the error function higher in a first region than in a second region, wherein the first region is prior to a patient neural response and the second region is after the patient neural response.

12. The system of claim 9, wherein, to remove the artifact, the processing circuitry is configured to pass the ECAP signal through a high-pass filter.

13. The system of claim 1, further comprising:

stimulation generation circuitry configured to:

generate a first train of electrical stimulation pulses at a first frequency to a first target tissue; and generate a second train of electrical stimulation pulses at a second frequency to a second target tissue different from the first target tissue, wherein:

at least some electrical stimulation pulses of the first train of electrical stimulation pulses are interleaved with at least some electrical stimulation pulses of the second train of electrical stimulation pulses, and wherein the first frequency is greater than the second frequency; and the processing circuitry is further configured to determine amplitude values for the first and second trains of electrical stimulation pulses as respective percentages of the estimated neural threshold.

14. The system of claim 1, wherein the stimulation parameter comprises a first stimulation parameter, and wherein the processing circuitry is configured to determine an initial value of a second stimulation parameter different from the first stimulation parameter based on ECAP characteristic values determined from different values of the second stimulation parameter.

15. The system of claim 1, wherein an implantable medical device or an external programming device comprises at least a portion of the processing circuitry.

16. The system of claim 1, wherein the estimated neural threshold is representative of a perception threshold of the patient for stimulation.

17. A method comprises:

controlling, by processing circuitry, delivery of a plurality of stimulation pulses to a patient, wherein each stimulation pulse of the plurality of stimulation pulses is at least partially defined by a different respective value of a stimulation parameter;

receiving, by the processing circuitry, evoked compound action potential (ECAP) signal information, wherein the ECAP signal information comprises ECAP signals sensed by sensing circuitry and elicited by the plurality of stimulation pulses;

determining, by the processing circuitry and based on the ECAP signal information, ECAP characteristic values for each of the ECAP signals elicited by the plurality of stimulation pulses;

determining, by the processing circuitry, a relationship between the ECAP characteristic values and the different respective values of the stimulation parameter; and determining, by the processing circuitry and based on the relationship between the ECAP characteristic values and the different respective values of the stimulation parameter, an estimated neural threshold of the patient for stimulation.

18. The method of claim 17, further comprising controlling stimulation circuitry to generate and deliver stimulation therapy based on the estimated neural threshold.

19. The method of claim 17, wherein the stimulation parameter is a stimulation amplitude, and wherein the method further comprises storing data on a storage device, the data defining a correlation curve defining the relationship between the ECAP characteristic values and the different respective values of the stimulation amplitude, wherein the correlation curve includes a first region where change in the value of the stimulation amplitude is defined in part by residual artifact, and a second region where change in the stimulation amplitude is defined in part by patient neural response, and wherein the first region is prior to the estimated neural threshold and the second region is after the estimated neural threshold.

20. The method of claim 17, wherein the ECAP characteristic values comprise the ECAP signal information with an artifact removed therefrom, and wherein the method comprises:

to remove the artifact, modeling the artifact as a sum of a single exponential component plus a linear component, wherein modeling the artifact comprises estimating a minimum of an error function by weighting the error function higher in a first region than in a second region, wherein the first region is prior to a patient neural response and the second region is after the patient neural response; and removing the sum from each ECAP signal.

21. A computer-readable storage medium comprising instructions that, when executed by processing circuitry, causes the processing circuitry to:

control delivery of a plurality of stimulation pulses to a patient, wherein each stimulation pulse of the plurality of stimulation pulses is at least partially defined by a different respective value of a stimulation parameter;

receive evoked compound action potential (ECAP) signal information, wherein the ECAP signal information comprises ECAP signals sensed by sensing circuitry and elicited by the plurality of stimulation pulses;

determine, based on the ECAP signal information, ECAP characteristic values for each of the ECAP signals elicited by the plurality of stimulation pulses;

determine a relationship between the ECAP characteristic values and the different respective values of the stimulation parameter; and determine, based on the relationship between the ECAP characteristic values and the different respective values of the stimulation parameter, an estimated neural threshold of the patient for stimulation.

* * * * *